US011376283B2

(12) United States Patent
Sokolov et al.

(10) Patent No.: US 11,376,283 B2
(45) Date of Patent: Jul. 5, 2022

(54) STEM CELL MATERIAL, COMPOSITIONS, AND METHODS OF USE

(71) Applicant: T-HELPER CELL TECHNOLOGIES, LLC, Moscow (RU)

(72) Inventors: Anatoliy Andreevich Sokolov, Moscow (RU); Antonina Ivanovna Kolesnikova, Moscow (RU); Andrei Igorevich Dovgii, Moscow (RU); Artem Andreevich Sokolov, Moscow (RU); Nikolay Vladimirovich Adrianov, Moskovskaya obl. (RU)

(73) Assignee: T-Helper Cell Technologies, LLC, Moscow (RU)

( * ) Notice: Subject to any disclaimer, the term of this patent is extended or adjusted under 35 U.S.C. 154(b) by 245 days.

(21) Appl. No.: 16/305,490

(22) PCT Filed: May 31, 2017

(86) PCT No.: PCT/RU2017/000381
§ 371 (c)(1),
(2) Date: Nov. 29, 2018

(87) PCT Pub. No.: WO2017/209658
PCT Pub. Date: Dec. 7, 2017

(65) Prior Publication Data
US 2020/0360440 A1    Nov. 19, 2020

(30) Foreign Application Priority Data
May 31, 2016    (RU) .............................. RU2016121458

(51) Int. Cl.
*A61K 38/18* (2006.01)
*A61K 38/20* (2006.01)
*A61K 35/28* (2015.01)
*A61K 9/00* (2006.01)
*A61K 45/06* (2006.01)

(52) U.S. Cl.
CPC ............ *A61K 35/28* (2013.01); *A61K 9/0048* (2013.01); *A61K 38/18* (2013.01); *A61K 38/1841* (2013.01); *A61K 38/2066* (2013.01); *A61K 45/06* (2013.01)

(58) Field of Classification Search
CPC ............................ A61K 38/18; A61K 38/1841
See application file for complete search history.

(56) References Cited

U.S. PATENT DOCUMENTS

| | | | |
|---|---|---|---|
| 5,486,359 A | 1/1996 | Caplan et al. | |
| 7,704,739 B2 | 4/2010 | Han et al. | |
| 8,287,853 B2 | 10/2012 | Cool et al. | |
| 8,318,197 B2 | 11/2012 | Steed et al. | |
| 8,361,485 B2 | 1/2013 | Naughton et al. | |
| 2002/0085996 A1 | 7/2002 | McIntosh et al. | |
| 2003/0103951 A1 | 6/2003 | Pittenger et al. | |
| 2004/0142861 A1 | 7/2004 | Mansbridge | |
| 2005/0164380 A1 | 7/2005 | Trisler et al. | |
| 2006/0083722 A1 | 4/2006 | Cibelli et al. | |
| 2006/0100124 A1 | 5/2006 | Mostoller | |
| 2007/0067860 A1 | 3/2007 | West et al. | |
| 2007/0243158 A1 | 10/2007 | Ronfard et al. | |
| 2007/0274960 A1 | 11/2007 | Harman et al. | |
| 2008/0206171 A1 | 8/2008 | Gueniche | |
| 2009/0136459 A1 | 5/2009 | Wu et al. | |
| 2009/0137040 A1 | 5/2009 | Cibelli et al. | |
| 2009/0169527 A1 | 7/2009 | Chopp et al. | |
| 2010/0226976 A1 | 9/2010 | Machluf et al. | |
| 2010/0310517 A1 | 12/2010 | Brem et al. | |
| 2010/0323027 A1 | 12/2010 | Lim et al. | |
| 2011/0003008 A1 | 1/2011 | Lim | |
| 2011/0129439 A1 | 6/2011 | Herrera Sanchez et al. | |
| 2011/0129447 A1 | 6/2011 | Meretzki et al. | |
| 2011/0177015 A1 | 7/2011 | Friedlander | |
| 2011/0212062 A1 | 9/2011 | Falanga | |
| 2011/0318315 A1 | 12/2011 | Aggarwal et al. | |
| 2012/0058089 A1 | 3/2012 | Hariri | |
| 2012/0107413 A1 | 5/2012 | Lim et al. | |
| 2012/0189585 A1 | 7/2012 | Giampapa et al. | |

(Continued)

FOREIGN PATENT DOCUMENTS

| | | |
|---|---|---|
| EP | 1 276 486 | 11/2010 |
| EP | 1 773 908 | 9/2012 |

(Continued)

OTHER PUBLICATIONS

Communication pursuant to Article 94(3) EPC dated Nov. 8, 2019 in European Patent Application No. 15866203.1.
Meirelles et al., "Mechanisms involved in the therapeutic properties of mesenchymal stem cells", Cytokine & Growth Factor Reviews, 2009, vol. 20, pp. 419-427.
Hwang et al., "Comparison of Cytokine Expression in Mesenchymal Stem Cells from Human Placenta, Cord Blood, and Bone Marrow", J Korean Med Sci, 2009, vol. 24, pp. 547-554.
Extended European Search Report dated Oct. 25, 2019 in European Patent Application No. 17807103.1.

(Continued)

*Primary Examiner* — Prema M Mertz
(74) *Attorney, Agent, or Firm* — Wenderoth, Lind & Ponack, L.L.P.

(57) ABSTRACT

Aspects of the invention relate to a novel mesenchymal stem cell line (hb-MSC), a culture medium conditioned by the hb-MSC line, and various hb-MSC compositions. The hb-MSC compositions may include a plurality of hb-MSCs, the hb-MSC conditioned medium, or a combination thereof. The hb-MSC compositions may also include one or more of an antimicrobial agent, a film-forming agent, an appropriate carrier, as well as other additives as determined by the application. Also described are methods of use for the hb-MSC cells, the conditioned medium, and the compositions, including methods of treating or preventing bovine mastitis.

24 Claims, 4 Drawing Sheets
Specification includes a Sequence Listing.

(56) References Cited

U.S. PATENT DOCUMENTS

| | | |
|---|---|---|
| 2012/0207705 A1 | 8/2012 | Kara |
| 2012/0251489 A1 | 10/2012 | Herrera Sanchez et al. |
| 2012/0263692 A1 | 10/2012 | Bertone |
| 2012/0276215 A1 | 11/2012 | Riordan et al. |
| 2012/0294949 A1 | 11/2012 | Johnstone et al. |
| 2012/0301538 A1 | 11/2012 | Gordon-Beresford et al. |
| 2012/0308535 A1 | 12/2012 | Gambacurta et al. |
| 2013/0039896 A1 | 2/2013 | Smith et al. |
| 2013/0058903 A1 | 3/2013 | Lee |
| 2013/0089514 A1 | 4/2013 | Cohen et al. |
| 2013/0110132 A1 | 5/2013 | Epstein et al. |

FOREIGN PATENT DOCUMENTS

| | | |
|---|---|---|
| JP | 2011-522553 | 8/2011 |
| RU | 2138246 | 9/1999 |
| RU | 2 292 212 | 1/2007 |
| RU | 2007 121 843 | 12/2008 |
| RU | 2341270 | 12/2008 |
| RU | 2372933 | 11/2009 |
| RU | 2432943 | 11/2011 |
| RU | 2512681 | 4/2014 |
| RU | 2 528 250 | 9/2014 |
| WO | 98/32450 | 7/1998 |
| WO | 01/32189 | 5/2001 |
| WO | 2008/060374 | 5/2008 |
| WO | 2008/070868 | 6/2008 |
| WO | 2009/150199 | 12/2009 |
| WO | 2011/042547 | 4/2011 |
| WO | 2011/052818 | 5/2011 |
| WO | 2011/063005 | 5/2011 |
| WO | 2013/132428 | 9/2013 |
| WO | 2014/039429 | 3/2014 |
| WO | 2015/028900 | 3/2015 |
| WO | 2016/089252 | 6/2016 |

OTHER PUBLICATIONS

Notification of Reason(s) for Refusal dated Oct. 29, 2019 in Japanese Patent Application No. 2017-547369, with English Translation.

Xing et al., "Inflammatory Microenvironment Changes the Secretory Profile of Mesenchymal Stem Cells to Recruit Mesenchymal Stem Cells", Cellular Physiology and Biochemistry, 2014, vol. 33, pp. 905-919.

Noort et al., "Angiogenic factors produced by fetal lung mesenchymal stromal cells", in Progenitor Cells and Hypoxia in Angiogenesis, 2011, Chapter 6, pp. 173-193.

Li et al., "Mechanical load modulates chondrogenesia of human mesenchymal stem cells through the TGF-β pathway", J. Cell. Mol. Med., 2010, vol. 14, No. 6A, pp. 1338-1346.

International Search Report, dated Apr. 21, 2016 in International Application No. PCT/RU15/000831.

Liu et al., "Cytokine interactions in mesenchymal stem cells from cord blood", Cytokine, 32:270-279 (2005).

International Search Report dated Oct. 19, 2017 in International (PCT) Application No. PCT/RU2017/000381.

Written Opinion of the International Searching Authority dated Oct. 19, 2017 in International (PCT) Application No. PCT/RU2017/000381.

Gnecchi et al., "Evidence supporting paracrine hypothesis for Aktmodified mesenchymal stem cell-mediated cardiac protection and functional improvement", The FASEB Journal, 20:661-669 (2006).

Pawitan, "Prospect of Stem Cell Conditioned Medium in Regenerative Medicine", BioMed Research International, vol. 2014:1-14 (2014).

Karaoz et al., "Characterization of mesenchymal stem cells from rat bone marrow: ultrastructural properties, differentiation potential and immunophenotypic markers", Histochem Cell Biol, 132(5):533-546 (2009).

Oshita et al., "Human Mesenchymal Stem Cells Inhibit Osteoclastogenesis Through Osteoprotegerin Production", Arthritis & Rheumatism, 63(6):1658-1667 (2011).

Gnecchi et al., "Paracrine action accounts for marked protection of ischemic heart by Akt-modified mesenchymal stem cells", Nature Medicine, 11(4):367-368 (2005).

Boomsma et al., "Mesenchymal Stem Cells Secrete Multiple Cytokines That Promote Angiogenesis and Have Contrasting Effects on Chemotaxis and Apoptosis", PLoS One, 7(4):1-8 e35685 (2012)

Chen et al., "Paracrine Factors of Mesenchymal Stem Cells Recruit Macrophages and Endothelial Lineage Cells and Enhance Wound Healing", PLoS One, 3(4):1-12 e1886 (2008).

Henson et al., "Karyotypic analysis of adult pluripotent stem cells", Histol Histopathol, 20:769-784 (2005).

Li et al., "Expression and secretion of interleukin-1β, tumour necrosis factor-α and interleukin-10 by hypoxia- and serum-deprivation-stimulated mesenchymal stem cells: Implications for their paracrine roles", FEBS Journal, 277:3688-3698 (2010).

Chen et al., "Conditioned Medium from Hypoxic Bone Marrow-Derived Mesenchymal Stem Cells Enhances Wound Healing in Mice", PLoS One, 9(4):1-12 e96161 (2014).

Mishra et al., "Cell-free derivatives from mesenchymal stem cells are effective in wound therapy", World Journal of Stem Cells, 4(5):35-43 (2012).

Singer et al., "Cutaneous Wound Healing", The New England Journal of Medicine, 341(10):738-746 (1999).

Cantinieaux et al., "Conditioned Medium from Bone Marrow-Derived Mesenchymal Stem Cells Improves Recovery after Spinal Cord Injury in Rats: An Original Strategy to Avoid Cell Transplantation", PLoS One, 8(8):1-15 e69515 (2013).

STEM CELL MATERIAL, COMPOSITIONS, AND METHODS OF USE

FIELD OF THE INVENTION

Compositions and methods consistent with embodiments of the present invention generally concern at least the fields of medicine, veterinary medicine, cell biology, molecular biology, and stem cell conditioned media. Embodiments of the present invention relate to stem cells, stem cell conditioned culture media, methods of obtaining stem cell conditioned culture media, as well as applications for stem cells and stem cell conditioned culture media. More particularly, embodiments of the present invention relate to compositions containing conditioned stem cell media as well as methods of making and using the compositions. The compositions of this application may be formulated and used for wound healing, wound and skin care, and other medical and veterinary applications, including reducing inflammation and irritation, as well as the treatment and prevention of bovine mastitis.

BACKGROUND

Mastitis is one of the most widespread and costly diseases affecting the dairy industry, with annual worldwide economic losses estimated to be in the billions of dollars. These losses arise from reduced milk yield, reduced compositional quality, lower product quality, milk discarded as a result of antibiotic residue, replacement costs for culled cows, costs associated with antibiotic and other treatments, as well as increased costs for veterinary services. For these reasons, the prevention and effective treatment of mastitis are major goals of the dairy industry.

Bovine mastitis refers to an inflammation of the mammary gland, which may be caused by infectious agents and their toxins, physical trauma or chemical irritants. In dairy cows, mastitis is typically caused by microorganisms, such as *Staphylococcus aureus, Streptococcus agalactiae, Streptococcus dysgalactiae, Streptococcus uberis* and *Escherichia coli*, among others. Trauma to the teat also renders it more susceptible to bacterial invasion, colonization, and infection. Conditions which contribute to trauma include: incorrect use of milking equipment, incorrect use of udder washes or cleaning compounds, wet teats, improper mixing or freezing of teat dips, frostbite, failure to prep cows or pre-milking stimulation for milk ejection, over milking, and insertion of mastitis tubes or teat cannulae. The incidence rate of mastitis may also be influenced by a number of other factors, such as housing conditions, stress, overall cow health, and genetic or hereditary predisposition to infections.

There are two general categories of mastitis: clinical and subclinical. A trained veterinarian can typically diagnose clinical mastitis based on abnormal milk, udder swelling, or systemic symptoms that include swollen quarters, watery milk, high fever, depressed appetite or elevated body temperature. As a result, milk from cows suffering from clinical mastitis is typically discarded. Subclinical (or hidden) mastitis does not typically manifest itself through clearly visible symptoms, and is therefore harder to diagnose and treat, but similarly leads to decreased milk production, bacteria in milk and undesirable changes to milk composition. Indeed, because of the cost associated with treating mastitis, subclinical mastitis is sometimes left untreated even when diagnosed, which can lead to lower quality milk (from cows with subclinical mastitis) being intermixed with normal milk in the bulk tank before being sold for public consumption. Moreover, mastitis always causes a certain irreversible destruction of milk producing tissue, which leads to a decrease in milk production. Bulk somatic cell count (SCC) is a generally accepted indicator of the overall health of the herd, wherein increased levels of mastitis generally correlate with an increase in the SCC. According to some studies, bulk tank somatic cell counts exceeding 700,000 could mean that between 25-50+% of the herd may be infected with mastitis.

Following diagnosis, clinical mastitis cases are typically treated with antibiotics. Antibiotics can be an effective treatment for clinical mastitis, particularly in the short term. However, the use of antibiotics to treat mastitis also has several disadvantages, including that milk from cows treated with antibiotics must be discarded for a period of several days, as milk that contains antibiotics is not suitable for human consumption. The discarding of milk from cows under treatment is one of the more expensive aspects of mastitis. Other drawbacks of treating mastitis with antibiotics include the negative impact on the cow's overall immune system, which can lead to decreased milk production. Another issue is that specialized knowledge and diagnostic techniques are required to select and treat mastitis with antibiotics, which increases the cost, time and labor investment by the veterinarian. There is also a concern that one or more bacterial strains will become resistant to the antibiotics currently used to treat mastitis. Another issue is that, although antibiotics can treat the clinical symptoms of mastitis, they do not address the degradation of milk alveoli caused by mastitis pathogens that lead to a decrease of milk production nor can they prevent future incidences of mastitis. In some cases, the treatment of clinical mastitis symptoms with antibiotics can lead to a loss of one (or multiple) milk producing quarter(s), which likewise leads to a reduction in milk production.

Commercial mastitis treatment products have been developed and used reduce the incidence of mastitis to some effect. However, the current commercially available mastitis treatment products also suffer from certain drawbacks. For example, iodine, hypochlorite, chlorine dioxide, and hypochlorous acid, which are some of the active ingredients in typical mastitis treatment products, have been linked to irritation of the teat skin, thus providing an opportunistic site for mastitis-causing bacteria.

There is thus a continuing need for compositions that are effective against mastitis and related conditions, are easy to use, and which reduce or avoid the drawbacks of currently used treatments. There is also a need for compositions that are not only effective in treating and controlling mastitis, but which also have prophylactic or preventive effect. And, there is a continuing need for compositions that are effective in wound care treatment and various wound applications, treating skin conditions, as well as those that are helpful in reducing inflammation and irritation, among other medical applications and conditions.

SUMMARY OF THE INVENTION

According to one aspect of the present invention, there is provided a unique line of mesenchymal stem cells derived from the bone marrow of a Wistar rat that has one or more of certain characteristics. For example, when $0.7 \times 10^6$ cells are seeded into a 75 cm² flask and cultured for at least 96 hours, the line of mesenchymal stem cells can: (a) produce at least 4.5 mM of lactate within 24 hours of media exchange; (b) produce at least 150 pg/ml of GRO/KC within 24 hours of media exchange; (c) produce less than 250 pg/ml of OPG following 24 hours after media exchange; or (d)

produce less than 80 pg/ml of TGF-β3 following 24 hours after media exchange. In accordance with another aspect, when $0.7 \times 10^6$ of the cells are seeded into a 75 cm² flask and cultured for at least 150 hours: (e) the pH of the culture medium decreases to below 7.0 within 24 hours of media exchange; or (f) the pH of the culture medium decreases by at least 0.4 units from the pH of the culture medium in the absence of cells within 24 hours of the culture medium exchange. The culture medium may be RPMI-1640 culture medium supplemented with 5% $CO_2$. In addition, the same stem cell line can undergo at least one population doubling at a pH of below 7.05. The stem cell line may also be characterized by the positive expression of CD29 and CD44 markers and negative expression of CD11b and CD45 markers.

A separate aspect of the invention relates to a conditioned medium, which can be prepared by maintaining a plurality of the unique stem cells in a culture medium for a specific conditioning period. In one aspect, the culture medium is RPMI-1640 supplemented with 5% $CO_2$. The cells may be maintained in the culture medium under various conditions, including an atmospheric concentration of $CO_2$ or in hypoxic conditions. According to aspects of the invention, the conditioning period may vary. For example, the conditioning period can be at least 12 hours, or it can be a period of time sufficient for the conditioned medium to contain at least 150 pg/mL of GRO/KC. In another aspect of the invention, the conditioned medium can contain at least one of the following: (a) at least 500 pg/mL of GRO/KC; (b) at least of 4000 pg/ml VEGF; (c) less than 250 pg/ml of OPG; or (d) less than 80 pg/ml of TGF-β3.

Another aspect of the invention relates to a composition, and methods for making the composition, that includes cells from the unique stem cell line or a culture medium conditioned by stem cells. The composition can also include one or more antimicrobial agent and/or one or more film-forming agent. The film-forming agent can be present at a concentration ranging from, for example, about 0.01% to about 2% (w/v). The antimicrobial agent can be present at a concentration ranging from, for example, about 0.001% to about 1.0% (w/v). The composition may further include one or more of a buffering agent, pH adjusting agent, a preservative, a skin conditioning agent, a surfactant, a foaming agent, a colorant, a chelating agent, and an appropriate carrier. In some aspects of the invention, the composition may be processed to remove some or all of the stem cells. In one aspect, the conditioned medium used in the composition includes one or more of VEGF, GRO/KC, IL-10, IP-10, TGF-β1 or TGF-β2. In another aspect, the composition may include a conditioned medium that contains at least 50 pg/mL of GRO/KC or at least of 500 pg/ml VEGF or at least 150 pg/ml of TGF-β2. In a further aspect, the composition may include a conditioned medium that has less than 500 pg/mL of OPG or less than 80 pg/ml of TGF-β3. According to aspects of the composition, the amount of VEGF in the composition is at least 5 times higher than the amount of OPG.

A further aspect of the invention relates to using one or more composition for treating or preventing mastitis. According to aspects of the invention, administering a therapeutically effective amount of the composition to a cow's udder or teat reduces the incidence of mastitis by at least 15% as compared to treatment with iodine based solutions. In another aspect, administering a therapeutically effective amount of the composition to a cow's udder or teat reduces the average somatic cell count of the cow's milk by at least 15% as compared to the average somatic cell count present prior to treatment with the composition. The method of administration for treating mastitis includes, but is not limited to one or more of a topical application, an oral application, or an injection. In topical applications, the composition may be applied to the cow's udder or teat by dipping or spraying. According to a separate aspect, the method of treating or preventing mastitis can include administering a second composition, which also contains at least the conditioned medium. In one aspect, the second composition is applied at the same time as the first composition. In a different aspect, the second composition may be applied at a different time, and may be administered by a different method, for example, orally.

In aspects of the invention, the cells, the conditioned medium or the composition may be applied to a suture, bandage, knitted mesh, implant, stent, graft, a wet wipe, or periodontal pad, or other applicator devices. The cells, the conditioned medium, or the composition has a variety of other uses beyond mastitis, including, for example, burn treatment, skin care, angiogenesis, vasculogenesis, healing of organs or tissue, cosmetics, tissue inflammation, bacterial infections, wound applications, diabetes, pharmaceutical and ophthalmological applications, scar reductions, stimulating hair growth, in immunotherapy applications and for immunocorrection therapy, skin, bone marrow, or organ transplants, the treatment of organs or tissue, or for the treatment of other illnesses of humans or animals.

BRIEF DESCRIPTION OF THE DRAWINGS

The above and/or other aspects of the present invention will become more apparent by describing in detail examples of embodiments thereof with reference to the attached drawings in which.

DETAILED DESCRIPTION

Figure 1:
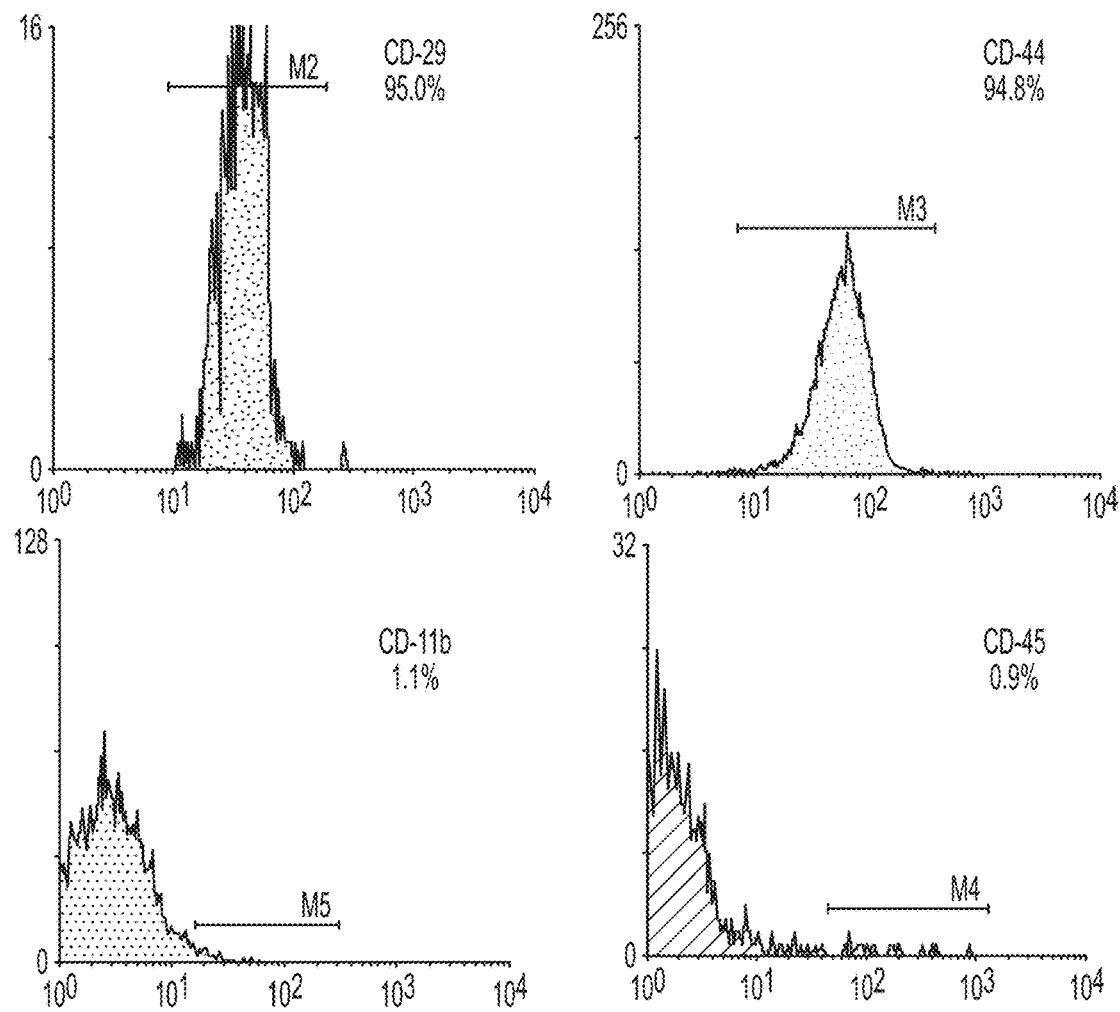
FIG. 1 illustrates the flow cytometry analysis of surface cell markers of hb-MSCs, including the marker type and the relative percent of markers.

Hereinafter, various examples of embodiments of the present invention will be explained with reference to the attached drawings. Aspects of the invention may be embodied in various forms without being limited to the embodiments set forth herein. It should be understood that any headings or subheadings used throughout the specification are provided for convenience only and shall not in any way limit the scope or meaning of the claims. It should be understood that, as used in the specification and the appended claims, the singular forms "a," "an" and "the" include plural referents unless the context clearly dictates otherwise. This application also incorporates by reference in its entirety PCT/RU2015/000831, filed Dec. 1, 2015.

One embodiment of the present invention relates to a novel mesenchymal stem cell line (hereinafter the "hb-MSC" line). A sample of the hb-MSC line has been deposited with the Russian National Collection of Industrial Microorganisms (VKPM) as accession number H-154. The cell line is deposited under the name MSCRO5P09. The expression of cell surface markers of the hb-MSC line is consistent with those of a mesenchymal stem cell.

Another embodiment of the present invention relates to a medium conditioned by hb-MSCs and the method of obtaining and using the same. The conditioned medium contains a myriad of biological products, small molecules and exosomes capable of multiple biological functions. The conditioned medium may be used as is, or may be used as part of a composition.

Other embodiments of the present invention relate to compositions, as well as methods of making and using the compositions, which may stimulate the subject's immune response, improve the regenerative and repair processes of damaged tissue, reduce inflammation, have an antimicrobial or antibacterial effect, treat and provide a prophylactic effect against infections such as mastitis, and are useful in wound healing and other applications. The hb-MSCs, hb-MSC conditioned media, hb-MSC compositions, and combinations thereof may be used with any subject, including humans and animals. For instance, the composition may be used to treat livestock, laboratory animals, companion animals or humans (collectively "mammals").

The hb-MSC compositions may include hb-MSCs, hb-MSC conditioned medium, or a combination thereof. Embodiments of the composition may further include: (1) one or more therapeutic agents; (2) other agents, additives or ingredients as described herein; and/or (3) one or more acceptable carrier. The agents, additives, and other ingredients to are selected according to the intended environment for use, and may be present in any suitable amount as necessary for the application. The hb-MSCs, the medium conditioned by hb-MSCs and the hb-MSC compositions may be used in any state, delivered using any method known in the art, and used in a variety of applications.

In one embodiment, the hb-MSC composition can be used to treat mastitis in lactating animals, such as dairy cows. For mastitis applications, the composition may be used prophylactically or for treatment of an existing infection. Use of the composition is not limited to treatment of mastitis, however, and the composition may be used for any of the purposes described herein, including, for example, to treat or protect against any infectious condition, for wound treatment, or for skin care applications. Embodiments of the compositions may also stimulating the body's immune response and decrease the number of microorganisms in the vicinity of the wound.

As used herein, and unless specified otherwise, the phrase "therapeutically effective amount" is intended to qualify the amount of the hb-MSC composition and/or antimicrobial agent, which will contribute to the goal of treating or preventing mastitis, wound healing, killing or limiting the effect of bacteria, or other disorders or conditions disclosed in this application. "Therapeutically effective" may also refer to an improvement in the severity of the disorder or the frequency of disease incidence as compared to subjects with no treatment. "Substantial improvement" means a more than 15% improvement.

Cells are passaged in vitro using a culture medium. Suitable media include, but are not limited to RPMI-1640, Dulbecco's Modified Eagle's Medium (DMEM), Ham's F12, Iscove's, McCoy's, or any other media that contains sufficient nutrients for cell growth. Such media can be prepared or obtained from commercial sources.

Depriving mesenchymal cells of their preferred growth environment typically results in decreased or stopped cell proliferation, loss of plastic adherence, and/or change in cell morphology. One important variable related to cell growth is the pH of the environment during cell proliferation. Typically, stem cells do not grow (or experience reduced proliferation rates) when conditions in culture deviate from physiological pH. For that reason, the culture medium typically acts as a buffer during cell culture. All cells produce and require small amounts of $CO_2$ for growth and survival. In some examples of culture media, dissolved $CO_2$ is in equilibrium with bicarbonate ions using the $CO_2$/bicarbonate reaction to buffer the pH of the medium. $CO_2$ dissolves freely into the medium and reacts with water to form carbonic acid. As the cells metabolize and produce more $CO_2$, the pH of the medium decreases. The optimal pH range of 7.2 to 7.4 can be maintained by supplementing the medium with sodium bicarbonate ($NaHCO_3$) and regulating the level of $CO_2$ in the atmosphere above the medium. The buffering capacity of the medium is determined by the amount of $NaHCO_3$. In general, 5% supplemental $CO_2$ is prescribed to achieve the optimal pH at a buffering capacity set by 1.2 to 2.2 g/L of $NaHCO_3$. As another example, to achieve the optimal pH at the buffering capacity set by 3.7 g/L of $NaHCO_3$, 10% supplemental $CO_2$ is prescribed. If the amount of supplemental $CO_2$ is below the buffering capacity of the medium, the pH of the medium may not be maintained at the appropriate levels, which can lead to senescence.

The cell culture medium may also include additional components such as vitamins, growth factors, hormones, proteins, sugars, and/or anti-oxidants, as necessary to support or maintain the desired cell culture. It should be understood that sera, such as fetal bovine serum (FBS), may be added. For example, 10% supplemental FBS could be added to the media, or plasma can be added in the same amount as animal serum. Alternatively, the cells could also be maintained and propagated in culture in the absence of supplemental serum and/or supplemental plasma. Media conditioned by cells may also be used in place of, or in addition to the culture media.

The hb-MSC line may be isolated from the bone marrow of a Wistar rat. The method of isolating the hb-MSC line generally includes at least: (1) obtaining Passage 1 (p1) cells from primary rat bone marrow cells; (2) seeding p1 rat mesenchymal stem cells in an appropriate flask; (3) a first incubation step, wherein the cells are incubated at a first predetermined $CO_2$ concentration for a first incubating time period; (4) a second incubation step, wherein the cells are incubated at a second predetermined $CO_2$ concentration for a second incubating time period; (5) collection of hb-MSCs.

Primary rat bone marrow stem cells can be harvested from the bone marrow of Wistar rat tibia or femurs according to well-known methods. Following cell harvest, the cell pellet may be re-suspended, seeded onto plastic tissue culture flasks and incubated in culture media (e.g., RPMI-1640 supplemented with 10% FBS) at 37° C. in a 5% $CO_2$ humidified atmosphere. The adherent cells grown to approximately 70% confluence are termed Passage No. 1 (p1).

In one embodiment, the first predetermined concentration of $CO_2$ may be set to match the $CO_2$ concentration prescribed for the buffering capacity of the media, as typically determined by the media manufacturer. For example, the first predetermined $CO_2$ concentration may be set to 5% when RPMI-1640 media is used for culture. In the same embodiment, the second predetermined concentration of $CO_2$ may be reduced by at least 50% from the $CO_2$ concentration prescribed for the buffering capacity of the media, as typically determined by the media manufacturer. For RPMI-1640 media the prescribed concentration of $CO_2$ is 5%. Therefore, according to one embodiment of the method, the second predetermined concentration of $CO_2$ should be set to below 2.5%. In another embodiment, the second predetermined concentration may be set to an atmospheric concentration of $CO_2$ (i.e. approximately 0.03% $CO_2$). One of ordinary skill in the art will understand that if the second predetermined concentration of $CO_2$ in the culture is increased, the second incubating time period may need to be increased (for example, one or more additional passages may be required) in order to isolate the hb-MSC line.

In one embodiment, the first incubating time period may be between zero to four cell passages. It should be understood that where the first incubating time period is zero passages, the first incubation step is skipped entirely. In another embodiment, the first incubating time period is a period between the number of hours required to achieve one population doubling (e.g., about 20-48 hours) to about 700 hours in culture. In one embodiment, the second incubating time period may be between one to eight cell passages. In a further embodiment, the second incubating time period is a period between the number of hours required to achieve one population doubling (e.g., about 20-48 hours) to about 2500 hours in culture. For example, the cells may undergo four passages in 0.03% $CO_2$ atmosphere in RPMI-1640 with 10% FBS. One of ordinary skill in the art will understand that the concentration of $CO_2$ may be adjusted during either incubation step as necessary.

A "passage" should be understood as the redistribution of cells, with or without dilution, from one culture flask to another culture flask containing fresh culture media. For example, a single cell passage may include: (1) seeding cells onto the surface of culture flask (e.g., approximately $2.0 \times 10^6$ cells on a 175 $cm^2$ surface area); (2) adding culture media (e.g., RPMI-1640); (3) setting a specified atmosphere of $CO_2$; (4) placing the culture flask in an incubator set to the appropriate temperature (e.g., 37° C.); (5) maintaining cells in the culture flask for predetermined period ("predetermined period of culture"); (6) supplying fresh culture media as necessary for cell growth; and (7) detaching and re-seeding cells.

For each passage, the cells are maintained in a culture medium where the predetermined period of culture is between about 30-700 hours. In one embodiment, the predetermined period of culture is less than 96 hours. In another embodiment, the predetermined period of culture is between about 96 to 168 hours. In yet a further embodiment, the predetermined period of culture is greater than 168 hours. Additionally, the predetermined period of culture may be based on cell confluence. In one embodiment, the predetermined period of culture is the time necessary for the cells to reach approximately 50% confluence. In another embodiment, cells are passaged after reaching between approximately 50% and 70% confluence. In a further embodiment, cells are passaged after reaching approximately 70% confluence.

The hb-MSC line may be isolated by culturing the cells in any number of dimensions (D). For example, the cells may be cultured using beads or microcarriers (OD), monolayers (2D), or 3D scaffolds. The hb-MSC line may also be isolated using a variety of systems. The hb-MSC line may be isolated using an open container system or a closed container system or a combination thereof. In one embodiment, the hb-MSC line may be isolated using a closed container system. In the closed container system, the cell culture flask is closed with an impermeable cap that can prevent access to supplemental $CO_2$. In another embodiment, hb-MSC line may be isolated using an open flask inside of a cell culture chamber that allows for control of $CO_2$ concentration. In another embodiment, the hb-MSC line may be isolated in a flask closed with a gas-permeable membrane, within a cell culture chamber that allows for control of $CO_2$ concentration. In one embodiment, a parallel plate bioreactor may be used to culture the hb-MSC cell line. In another embodiment a 3D scaffold bioreactor may be used to culture the hb-MSC cell line. In another embodiment, the hb-MSC cell line may be cultured using microcarriers within a stirred tank reactor.

One of ordinary skill in the art will understand that the various methods of culturing cells described above are provided as examples only and may not be used to limit the scope of any claims. One of ordinary skill in the art also will understand that the procedures, incubation periods, culturing periods, media, sera or $CO_2$ concentrations and other variables may need to vary to account for the behavior of cells during culturing.

Another embodiment of the present invention relates to the unique hb-MSC line. Cell surface marker expression can be used to confirm the mesenchymal nature of this line. Cell surface markers may be identified using any suitable method, including, for example, flow cytometry. As described in Example 4 and shown in FIG. 1, the method of obtaining hb-MSCs does not result in a change to the surface markers of the hb-MSCs, which can lead to a conclusion that hb-MSCs exhibit surface markers consistent with those of a rat bone marrow mesenchymal stem cell.

Figure 2:
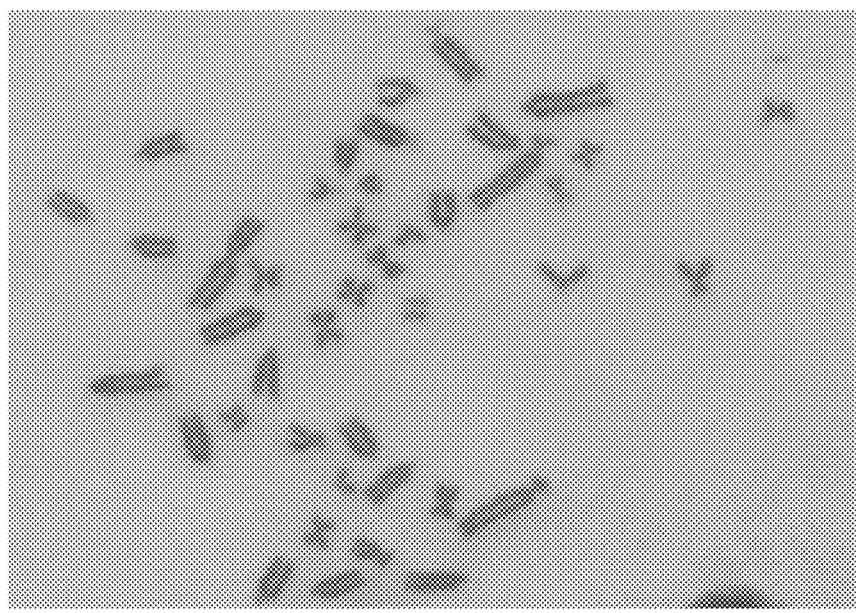
FIG. 2 illustrates Giemsa stained chromosomes from hb-MSCs at Passage No. 9 (p9).
Figure 3:
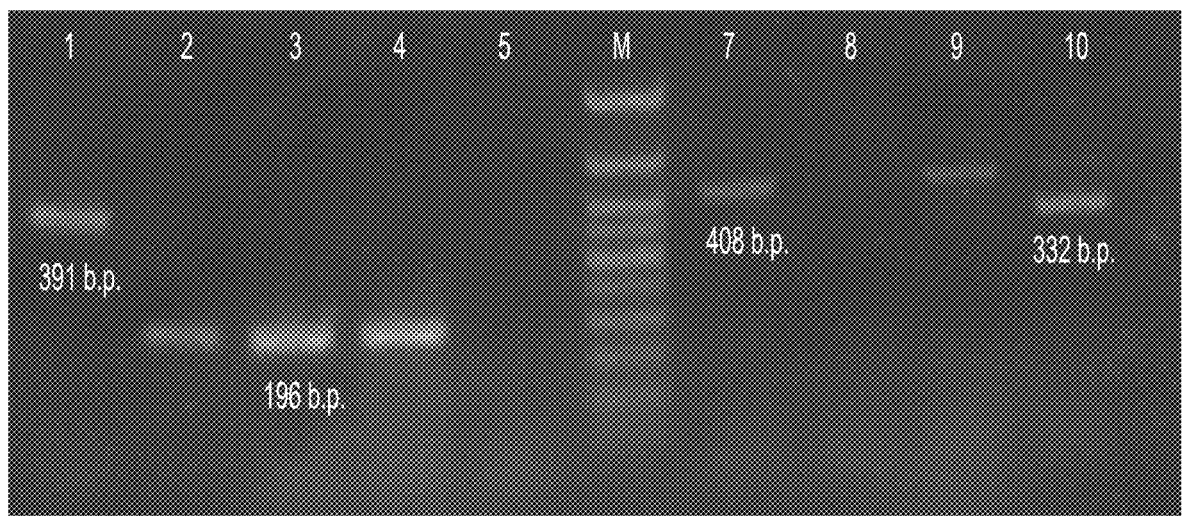
FIG. 3 illustrates the electrophoretograms of the PCR analysis of hb-MSCs and controls.

FIG. 2 illustrates the Giemsa stained chromosomes from hb-MSCs at Passage No. 9 (p9), while FIG. 3 illustrates the results of polymerase chain reaction (PCR) analysis. COX-1 and VN1R1 genes were used as markers for rat mitochondrial and nuclear DNA, respectively. At Passage No. 9, the karyotype is normal diploid (i.e. 2n=42). As described in Example 1 below, PCR analysis of the cell line confirmed that these are rat cells. One of ordinary skill in the art will understand that cells may be maintained for any number of passages, provided that karyotype analysis confirms the genetic stability of the cells.

The hb-MSC line differs significantly from other lines of stem cells obtained from rats, as can be illustrated using a number of different characterization methods. Rat mesenchymal stem cells obtained under standard conditions were cultured to show the differences between the typical rat mesenchymal stem cell and the unique hb-MSC line. The typical rat mesenchymal cell line prepared for purposes of this comparison was termed the rb-MSC line. To obtain the rb-MSC line, p1 rat mesenchymal cells were passaged according to standard conditions known in the art, as described in Example 2.

Example 5 (and FIG. 6) shows the difference between the pH of the medium of the hb-MSC and the rb-MSC line, which can be used to differentiate between the two lines. In another comparison, the hb-MSC line may be differentiated from the rb-MSC line by the total concentration of lactate in culture. Another way to differentiate the hb-MSC line from the rb-MSC line is by comparing various factors found in media conditioned by each respective line, as explained in Example 6 (and shown in Table 3). Of course, the hb-MSC line may also be characterized by other methods known to one of ordinary skill in the art.

Embodiments of the invention also relate to cells or cell lines differentiated from hb-MSCs. The cell lines can include adipocytes, chondrocytes, osteocytes, or other cells. Methods of differentiating to adipocytes, chondrocytes, osteocytes are well known in the art. Methods for genetically modifying stem cells are also well known. Stem cell lines made from genetically modified hb-MSCs and any cell lines differentiated from the genetically modified hb-MSCs are also within the scope of the invention.

One of ordinary skill in the art will understand that the various methods of characterizing hb-MSCs are provided for illustrative purposes only. Embodiments of hb-MSCs do not have to satisfy each of the various disclosed characterization methods, and some embodiments may satisfy only one or more of the characterization methods disclosed herein.

One embodiment of the invention relates to a culture medium conditioned by hb-MSCs, hereinafter termed "hb-MSC conditioned medium." In one embodiment, the conditioned medium may be produced by: (1) seeding a plurality of hb-MSCs into an appropriate flask; (2) providing a culture medium; (3) maintaining the hb-MSCs in culture media for a conditioning period; and (4) collecting the conditioned medium. The conditioning period may be hours, days, or even weeks, during which time the culture medium becomes enriched with biological products. When appropriate (e.g., once the medium is conditioned so that biological products such as growth factors, proteins and vesicles have reached desirable levels in the medium), the conditioned medium can be collected. For example, the conditioned medium may be collected after the hb-MSCs have been cultured for 3, 6, 24, 30, 48, 48, 54, 72, 96, 120, 144, 168, 192, 216, 240, 264, 288, 312, or 366 hours, or some other time period. One of ordinary skill in the art will also understand that other methods of conditioning a culture media are available, including by way of a bioreactor. In some cases, if a bioreactor is used, the method of conditioned media collection may depend on the chosen cell culture method. One of ordinary skill in the art will understand that the chosen bioreactor configuration will dictate the cell growth and the conditioned media collection protocol. In one embodiment, the use of a bioreactor is coupled with a batch collection of cell culture media, at a specified time period. For example, the conditioned media may be collected once the hb-MSCs have been cultured in a bioreactor for 3, 6, 24, 30, 48, 48, 54, 72, 96, 120, 144, 168, 192, 216, 240, 264, 288, 312, or 366 hours, or some other time period. In another embodiment, a method of continuous collection of the conditioned media and continuous replenishment of the fresh culture media may be chosen. In this particular example, the collection time and rate may be based on a series of cell culture factors, such as pH, lactate concentration, dissolved $O_2$ concentration, or the concentration of a specific cytokine in the conditioned medium.

The conditioned media obtained by culturing hb-MSCs may be processed under sterile conditions or sterilized as needed. One of ordinary skill in the art will understand that collection of the conditioned medium prior to the attachment of cells to the flask used for culture will result in the removal of cells with the growth medium, which may not be desired depending on the application.

In one embodiment, the hb-MSCs may be re-used to condition additional media by adding culture media to the hb-MSCs after removal of the conditioned medium. One of ordinary skill in the art will understand that the number of times that the cells may be reused depends on the number of hours used to condition the medium as well as the confluence of the cells. It should be understood that the hb-MSC conditioned medium collected over different time periods (e.g., every 3, 6, 24, 30, 48, 48, 54, 72, 96, 120, 144, 168, 192, 216, 240, 264, 288, 312, or 366 hours, or some other time period), conditioned medium collected by re-using hb-MSCs within a single passage, or medium collected from different passages of hb-MSCs may be combined for purposes of forming a single hb-MSC conditioned medium. It should also be understood that the culture of hb-MSCs by other means, such as a 3D scaffold or a stirred tank bioreactor, may require a continuous media exchange process, and such methods of conditioning media and collection of conditioned media are also within the scope of the invention.

Media conditioned by any cell may include various biological products secreted, excreted, released, or otherwise produced during culture. For example, the conditioned medium may include biological products, such as, growth factors, anti-inflammatory factors, signaling factors, hormones, regulatory factors, enzymes, vesicles including exosomes, or any other compounds. The method of cell culture and the pH of the media may impact the type and amount of biological products released by the cells. It should also be understood that the concentration of cells initially seeded may impact the amount of biological products present in the conditioned media. It will also be understood that the addition of supplemental sera will impact the starting concentration of factors in the media prior to being conditioned, as the sera contains certain amounts of various biological products. Measuring the concentration of these factors in medium conditioned by hb-MSCs shows that this medium is significantly different from medium conditioned by rb-MSCs. Commercially available assays can be used to measure the concentrations of factors produced by the cells (e.g., assays available from EMD Millipore or Eve Technologies). It should be understood that the exact measurement will depend on the antibody pairs used in the assays, and thus the detected concentration of factors may vary depending on the assay or measurement technique used. Example 6 describes a comparison of factor concentrations of the rb-MSC and hb-MSC lines at specified time periods.

In one embodiment, the conditioned medium may be formed by maintaining hb-MSCs in a $CO_2$ concentration prescribed for the buffering capacity of the media, as typically determined by the media manufacturer. For RPMI-1640 media, the prescribed concentration of $CO_2$ is 5%. In another embodiment, the conditioned medium may be formed by maintaining hb-MSCs in a concentration of $CO_2$ that is reduced by at least 50% from the $CO_2$ concentration prescribed for the buffering capacity of the media, as typically determined by the media manufacturer. In another embodiment, the conditioned medium may be formed by maintaining hb-MSCs at an atmospheric concentration of $CO_2$ (i.e. 0.03% $CO_2$).

In one embodiment, the conditioned medium may be formed by maintaining hb-MSCs in an atmospheric concentration of $O_2$ (i.e. 17%). In another embodiment, the conditioned medium may be formed by maintaining hb-MSCs in a concentration of $O_2$ reduced below 10%. In another embodiment, the conditioned medium may be formed by maintaining hb-MSCs in a concentration of $O_2$ reduced below 2%. The use of a lowered concentration of $O_2$ (hypoxic conditions) may be used, for example, to mimic the bone marrow environment in vivo.

In some embodiments, the conditioned medium may be used in concentrated form. For example, the conditioned medium may be concentrated by a factor between 1 and 100 using any known method in the art. The appropriate concentrations required will depend on the application of the conditioned medium.

In one embodiment, the neat collected conditioned medium is further processed to add/remove and/or concentrate/dilute specific biological products. The methods used for product isolation and purification should be selected such that optimal biological activity is maintained. For example, it may be desirous to purify a growth factor, regulatory factor, peptide hormone, antibody, exosome or any other desired biological compound. Such methods include, but are not limited to, gel chromatography, ion exchange, metal chelate affinity chromatography, high pressure liquid chromatography (HPLC), hydrophobic interaction chromatography, or centrifugation. In another embodiment, the exosomes or any other vesicles present in the conditioned medium may be concentrated in the conditioned medium or removed from the conditioned medium.

In another embodiment, the conditioned medium can be lyophilized. The lyophilized conditioned medium can be reconstituted utilizing any appropriate diluent including, without limitation, normal saline, phosphate buffered saline, cell culture media, conditioned cell culture media, water, or mixtures thereof. The conditioned medium may be reconstituted in the same concentration as the original conditioned medium. In a separate embodiment, the lyophilized conditioned medium can be reconstituted in a more concentrated form as compared to the original conditioned medium with the concentration factor varying from 1 to 100. One of ordinary skill in the art will understand that the reconstitution of the conditioned medium for a composition may also result in a change to the pH, viscosity, or other physical properties as desired for the specific application.

The hb-MSC line may be used to condition a wide variety of culture media. In some embodiments, the culture media may also be supplemented with additional fetal serum and/or plasma. In one embodiment, the medium is conditioned in the presence of 20% FBS. In another embodiment, the medium is conditioned in the presence of 10% FBS. In another embodiment, the medium is conditioned in the presence of 7% FBS. In another embodiment, the medium is conditioned in the presence of 3% FBS. In an alternate embodiment, the medium is conditioned in the absence of FBS. In other embodiments, after the cells have reached a specific confluence, a lowered concentration of serum or serum-free media may be used as a replacement, to form a low-serum or a serum-free conditioned medium.

Another embodiment of the present invention relates to hb-MSC compositions. The hb-MSC compositions may include therapeutically effective amounts of hb-MSCs, hb-MSC conditioned medium, or a combination thereof, wherein the amount will vary depending on the desired application. In another embodiment, lyophilized hb-MSC conditioned medium may be used in the composition. The total amount of hb-MSC conditioned medium in the composition should be selected such that the composition is effective for the desired application, and can vary between 0.00001 to 99.99% by weight to volume. Embodiments of the hb-MSC composition may further include: (1) one or more therapeutic agents; (2) other agents, additives or ingredients as described herein; and/or (3) one or more acceptable carrier.

Embodiments of the hb-MSC composition may include hb-MSC conditioned medium combined with hb-MSCs, rb-MSCs, or other cells selected on the basis of the application/purpose of the medium or composition. For example, the cells that may be added to the hb-MSC composition may include autologous cells, allogeneic cells or xenogeneic cells.

In certain embodiments, the hb-MSC composition may include hb-MSCs or hb-MSC conditioned medium combined with any other conditioned medium or any combination of conditioned media in any desired ratio. The hb-MSC composition may also include hb-MSCs or hb-MSC conditioned media in combination with media conditioned by autologous cells, allogeneic cells or xenogeneic cells. In another example, the hb-MSC conditioned media may be combined with media conditioned by human mesenchymal stem cells.

In one embodiment, the hb-MSC composition may include one or more antimicrobial agent that is effective against bacteria and other microorganisms, including mastitis-causing pathogens. The hb-MSC composition may also include a film-forming agent, which forms a persistent and continuous protective barrier film over the target application site, protects the target site from physical exposure to pathogens or other microorganisms for a predetermined period of time, and may act as a controlled release layer for certain active ingredients. Embodiments of the hb-MSC composition may have both an immediate and/or a prolonged effect, in particular when the composition includes both an antibacterial and a film-forming agent. Embodiments of the hb-MSC composition may also include one or more of the following agents, additives, or ingredients: a buffering or pH adjusting agent, a preservative, a skin conditioning agent, a surfactant, a foaming agent, a viscosity-modifier, a colorant or opacifying agent, a chelating agent, an acceptable carrier, and/or any combinations thereof.

One of ordinary skill in the art will understand that the ingredients, and their effective amounts, should be selected in a way that ensures the ingredients' continuing efficacy and viability, in particular with respect the stem cell conditioned medium, any film-forming agent, and/or any antimicrobial agent. For example, if adding an ingredient would result in the denaturing of the biological materials of the stem cell conditioned medium, the specific ingredient may not be a good candidate for the specific formulation of the composition. Similarly, the addition of a specific ingredient should not interfere with the formation of a persistent and continuous barrier film at the target area (if the composition includes a film-forming agent) and, in certain embodiments, should not render the film unsafe for animal or for human consumption.

In one embodiment, the hb-MSC composition may contain one or more antimicrobial agent. As used herein, and unless specified otherwise, the term "antimicrobial" refers to an effect that kills or helps kill micro-organisms or inhibits their growth, and includes, for example, an antibacterial, antifungal, antiseptic, antiviral, bactericidal, or bacteriostatic effect. In this application, the term "antimicrobial agent" refers to antimicrobial agents that are used for the treatment of a subject. By contrast, as one of ordinary skill in the art will understand, a "preservative" (discussed below) is used to keep the composition itself free of contamination, such as, by bacteria, viruses, mycoplasma, or fungi.

Examples of antimicrobial agents that may be used in embodiments of the hb-MSC composition include: an aminoglycoside (e.g., Neomycin), tetracycline (e.g., Doxycycline), β-lactams (e.g., Amoxicillin, Cephalexin), peptide based (e.g., Bacitracin), glycopeptide based (e.g., Vancomycin) Lantibiotics (e.g., Ancovenin, Cinnamycin, Duramycin, Epidermin, Gallidermin, Gardimycin, Nisin), polymyxins (e.g., Colistin), colicins, microcins enzyme-based antibacterials (e.g., lysostaphin), fluoroquinolones (e.g., Ciprofloxacin), chlorhexidine, 2-bromo-2-nitro-1,3-propanediol (Bronopol), or additional antimicrobial agents as dictated by the application. The hb-MSC composition should contain a therapeutically effective amount of one or more antimicrobial agent, the amount of which will vary depending on the class of antimicrobial and the desired application, but each antimicrobial agent should generally be in the range of between about 0.001% to about 1.0% by weight to volume (w/v). It should be understood that derivatives and structural analogs of the above-disclosed antimicrobial agents are also within the scope of the invention. It should also be noted that, in certain embodiments, the hb-MSC composition may include two or more antimicrobial agents.

In one embodiment, the hb-MSC composition includes Nisin as the antimicrobial agent. Nisin is a short, nontoxic peptide (Lantibiotic) that exerts a bactericidal effect on many gram-positive organisms, including bacteria responsible for bovine mastitis, such as *Staphylococcus aureus, Streptococcus agalactiae, Streptococcus dysgalactiae, Streptococcus uberis*. Nisin can also exert a bactericidal effect on some gram-negative organisms, in particular when combined with a chelating agent, such as ethylenediaminetetraacetic acid (EDTA). The hb-MSC composition may include a therapeutically effective amount of Nisin, such, for example, 0.001 to about 0.01% (w/v).

In one embodiment, the hb-MSC composition may also include one or more film-forming agents, which form a persistent and continuous film or barrier over the target application site (such as the teat or udder of a cow), and protects the target site from physical exposure to pathogens for a predetermined period of time. The film-forming agent may also form a barrier at the open end of the teat canal to assist in stopping the penetration of mastitis causing pathogens. Additionally, the film-forming agent in the hb-MSC composition may act as a controlled release layer, prolonging the action of the conditioned medium, any antimicrobial, or other agents, if such agents are included in the composition. The inclusion of the film-forming agent in the hb-MSC composition may reduce the incidence of both contagious and environmental mastitis in dairy herds.

Compositions according to the present invention may also include one or more viscosity modifiers to adjust the viscosity of the composition. It should be understood that the addition of film-forming agents may modify the viscosity of the hb-MSC composition. Modification of the viscosity of the composition may be beneficial for application to a target site, e.g., when using a teat dip. While all of the materials listed below may be used for both film-forming and viscosity modifying purposes, the quality of the film formed at the target site need not necessarily be correlated to the viscosity modifying property of the material. For convenience, the term "rheology modifier" may be used to refer generally to both film-forming agents and viscosity modifying agents. Typical film-forming/viscosity modifying agents include cellulose derivatives (e.g., methyl cellulose, ethyl cellulose, hydroxypropyl cellulose, hydroxyethyl cellulose, carboxyethyl cellulose, or carboxymethyl cellulose), polyvinyl pyrrolidone, acrylate polymers, polyvinyl alcohol (PVA), silicones, latexes, gums (e.g., xanthan gum, guar gum, gum arabic, johannistree gums), starches and starch derivatives (e.g., hydroxyethyl starch), arabinoxylans, glucomannanes, glycerin, sodium alginate, or mixtures, derivatives and structural analogs thereof. It should be understood that the cross linking of polymers described above is within the scope of the present invention. In one embodiment, the film-forming agent is methyl cellulose at a concentration ranging from 0.1% to 1.5% (w/v).

One of ordinary skill in the art will understand that the chemical composition of the viscosity modifying agent or film-forming agent will depend on the desired application. For example, for mastitis applications it may be desirous to utilize water-soluble additives to facilitate the removal of the composition from the teat and/or udder prior to milking. In another example, a water insoluble additive may be used to prevent the removal of the hb-MSC composition by rinsing with water. In another embodiment, the hb-MSC composition may (but does not have to) include materials generally regarded as safe (GRAS) or permitted food additives.

The amount of film-forming agents and viscosity modifying agents in the hb-MSC composition may be adjusted based on the particular application. For example, in topical anti-mastitis applications, the amount of film-forming agents and viscosity modifying agents in the composition should be sufficient to form a persistent and continuous film or barrier over the target application site. Likewise, one of ordinary skill in the art will understand that, for certain compositions, such as those that are injected, the composition should not include any viscosity modifying or film-forming agents. And, for other applications, such as personal care products, an intermediate or medium viscosity composition may be useful. The film-forming agents and viscosity modifying agents can each be used at a level of between 0 to about 5% (w/v), or between about 0.01 to about 2% (w/v), or between about 0.05 to about 1% (w/v), and are used to create approximate viscosities of 2 to 5000, 10 to 1000, or 25 to 500 cP. However, one of ordinary skill in the art will understand that compositions may be formulated for a wide variety of applications by altering the amount of viscosity modifying agents.

Surfactants may be added to embodiments of the hb-MSC composition to help formulate the composition for a specific intended environment or application. Surfactants may also help increase overall detergency of the formula, solubilize or emulsify some of the organic ingredients that otherwise would not dissolve or emulsify, and facilitate penetration of active ingredients into the intended target application site, such as the skin on teats of a dairy cow. In some embodiments, surfactants may be used to assist in the formation of nanoparticles or vesicles that include an embodiment of the hb-MSC composition of the present invention, which may improve the penetration of the composition into the surface of the target site. Embodiments of the hb-MSC composition may include one or more surfactants, each in the amount between 0.01% and 6% (w/v). Suitable surfactants include, but are not limited to, one or more of the following: polysorbates (Tween series), octylphenoxy polyethoxy ethanol (Triton-X series), poloxamers (PLURONIC F-68), glucosides (e.g., n-octyl, lauryl, or n-decyl), cationic agents (e.g., lauramine oxide); zwitterionic agents (e.g., cocoamidopropyl betaines), fatty acids, glycerides, monoglycerides (e.g., glycerol monolaurate), deoxycholate and esters of deoxycholate, as well as mixtures, derivatives and structural analogs thereof. In one embodiment, the surfactant is Triton X-100 (0.01 to 1% w/v).

In some embodiments, the surfactant may function to reduce the surface tension of the composition, or to increase the colloidal stability of the composition leading to foaming. Suitable foaming agents include sodium laureth sulfate, sodium lauryl sulfate or ammonium lauryl sulfate. In another embodiment, an anti-foaming agent may be added to disrupt or destabilize the foam micelles. Suitable antifoaming agents can include silicone based antifoamers such as simethicone. It should be understood that, in this application, the term "foaming agents" includes both foaming and anti-foaming agents.

In one embodiment, the hb-MSC composition may include one or more chelating agents, such as, for example ethylenediaminetetraacetic acid (EDTA) and/or its alkali salts, which, when used in combination with an antimicrobial agent, can increase effectiveness against gram-negative bacteria. Other chelating agents that may be used include, for example, other alkyldiamine tetraacetates, as well as ethylene glycol-bis(β-aminoethyl ether)-N,N,N',N'-tetraacetic acid (EGTA), aspartic acid, and citric acid, as well as derivatives, mixtures or structural analogs thereof. Generally, each chelating agent may constitute from 0.005% to about 1.00% (w/v), but other amounts may be used as necessary for the application. The chelating agents may be used alone or as a combination of several chelating agents. In one embodiment, the chelating agent is EDTA at a concentration ranging from 0.03% to 0.3% (w/v).

One or more skin conditioning agents such as emollients and humectants may also be optionally used in hb-MSC compositions to make skin softer and more pliable. These conditioning agents also help increase the permeability of skin, replenish oils and fats, promote the retention of moisture in skin, and help prevent skin damage due to adverse weather/environmental conditions or mechanical damage. In a mastitis-related application, the mechanical damage may be caused by, for example, the use of an automated milking apparatus. Embodiments of the hb-MSC composition may include one or more skin conditioning agents, each in the amount between 0.1% and 30% (w/v). Examples of skin conditioning agents include one or more of glycerin, propylene glycol, polyethylene glycol, mineral oil, petroleum jelly, sorbitol, lactylate, or mixtures, derivatives and structural analogs of these agents. Other skin conditioning agents may include one or more of D-Panthenol, Hyaluronic acid, Polyquaternium-7, Stearic Acid, Silk amino acid, Aloe Vera, shea butter and coco butter. In one embodiment, the skin conditioning agent is glycerin, in a concentration of about 1.0% to about 12% (w/v). In another embodiment, the skin conditioning agent is hyaluronic acid, at a concentration of between about 0.02% and about 3.0% (w/v). It should be understood that, in some cases, the skin conditioning agent may also be used as the carrier (e.g., in creams), in which case the concentration of the carrier material may be as high as 99%. One of ordinary skill in the art will understand that other known skin conditioning agents may also be used as part of one or more embodiments of the composition of the present invention. One of ordinary skill in the art will also understand that, for certain applications, such as those wound treatments, the composition may not need to include any skin conditioning agents.

Embodiments of the hb-MSC composition may also include an effective amount of additional ingredients such as one or more sunscreen, itch-relief or numbing agents. These include, but are not limited to, titanium dioxide, zinc oxide, calamine, mint, menthol, camphor, antihistamines (e.g., diphenhydramine), corticosteroids (e.g., dexamethasone, hydrocortisone), or local anesthetics (e.g., lidocaine).

The pH of the hb-MSC composition may be adjusted by the addition of acidic, basic or buffering components. For mastitis and wound healing, the pH of the hb-MSC composition should be selected in a way that ensures the ingredients' continuing efficacy and viability, in particular with respect the stem cell conditioned medium, the film-forming agent, and/or the antimicrobial agent. In one embodiment, the pH of the disclosed composition is between 6.5 and 7.5. Any buffering or pH adjusting agent that is known to be compatible for use with stem cell conditioned media can be used as a buffer in the hb-MSC composition. Examples of suitable pH adjusting agents include, but are not limited to, citric acid, sodium carbonate, or sodium bicarbonate, sodium acetate, sodium dihydrogen phosphate, sodium hydrogen phosphate, sodium phosphate, and tris(hydroxymethyl)-aminomethane, boric acid, or mixtures thereof. As discussed above, the culture media used for cell growth can also act as a buffer. Another buffer that may be used is phosphate buffered saline.

In a further embodiment of the invention the composition can include an isotonic agent, such as, for example, a salt (e.g., sodium chloride), a sugar or sugar alcohol, an amino acid (e.g., L-glycine, L-histidine, arginine, lysine, isoleucine, aspartic acid), or mixtures derivatives, and structural analogs thereof. Any sugar or sugar alcohols can include fructose, glucose, mannose, sorbose, xylose, mannitol, sorbitol, galactitol, xylitol, and arabitol. The sugars or sugar alcohols mentioned above may be used individually or in combination. There is no fixed limit to the amount used, as long as the sugar or sugar alcohol is soluble in the liquid preparation and does not adversely affect the stabilizing effects achieved using the methods of the invention. Generally, each isotonic agent may constitute from about 0.001% to about 5.00% (w/v), but other amounts may be used as necessary for the application. In one embodiment, the isotonic agent is sodium chloride at a concentration of about 0.05% to about 1.5% (w/v).

A colorant, dye or opacifier is optionally included in hb-MSC compositions. In mastitis control applications, the addition of color to the target site (e.g., a teat) provides a visual indicator that a treatment has been applied. Examples of suitable dyes include, but are not limited to, any of the artificial colorings generally permitted in food, such as FD&C Blue #1, FD&C Green #3, FD&C Red #40, FD&C Yellow #5, and FD&C Yellow #6, or mixtures thereof. In another embodiment the lakes of the FD&C dyes may be used to provide a color suspension to the composition. In one embodiment, Titanium dioxide ($TiO_2$) can be used in combination with the various dyes. In another embodiment, the colorant may be present as a microbead or a microsphere, which may be fluorescent. Generally, the colorant is added in the lowest possible amount as dictated by the application.

In an embodiment, the hb-MSC composition includes an acceptable carrier. The acceptable carrier can take the form of, for example, a liquid, viscous liquid, cream, aerosol, lotion, ointment or hydrogel. In another embodiment, the hb-MSC composition may be formulated into particles on the nano to micro scale. One of ordinary skill in the art will understand that carriers may include aqueous excipients (such as culture media or water), non-aqueous excipients, oils, standard fatty substances, conventional gelling agents, suspension agents, emulsifiers, and hydrophilic or lipophilic active agents. Of course, one of ordinary skill in the art will understand that the "acceptable carrier" may include a mixture of two or more carriers and/or other ingredients. The amounts of these various ingredients will vary depending on the use of the hb-MSC composition and the effect desired. For example, the carrier may be added to achieve or enhance the desired effect of the other additives/agents in the composition, such as the antimicrobial agent, the film-forming agent, or the conditioned medium. It should be understood that acceptable carriers may also carry out a functional role (e.g., as a skin conditioning agents). This dual function may be exploited for purposes of formulation for a particular application. The carrier can also be used to dilute or solubilize the components of the composition. In particular, film-forming agents (such as methyl cellulose) are typically formulated as a 1 to 2 weight percent relative to the volume of the aqueous component. In one embodiment, the composition contains at least about 10% carrier material based on w/v. In a further embodiment, the composition contains at least about 50% carrier material based on w/v. In other embodiments, the acceptable carrier comprises at least about 75% of the composition, based on w/v. In another embodiment, the acceptable carrier comprises between about 90 and 99% of the composition, based on w/v.

In one embodiment, hb-MSC compositions can be kept free of contamination by bacteria, viruses, mycoplasma, or fungi by sterile processing conditions during cell culture and processing. In another embodiment, the hb-MSC compositions may contain one or more preservatives in an amount that is effective to provide a level of antimicrobial activity within the composition, or reduce the degradation of antimicrobials (or other additives) in the composition. In some embodiments the preservatives may limit secondary bacterial, mycotic, or amoebal infections caused by contamination of solutions. In other embodiments the addition of preservatives prolongs the shelf life of the hb-MSCs, the hb-MSC conditioned media, or the hb-MSC composition by preventing biodegradation and maintaining potency. In one example, the preservatives can include detergents, oxidants, chelating agents, or metabolic inhibitors including pentavalent antimonials, quaternary ammoniums, and organomercurials. Other examples of preservatives include thimerosal, cresols, formalin, benzalkonium chloride, paraben, methyl paraben, or ethyl paraben, carboxylic acids and carboxylate salts, alcohols, or mixtures, derivatives and structural analogs thereof. The alcohol, in embodiments, may be ethyl alcohol, isopropyl alcohol or benzyl alcohol. Generally, the one or more preservative may each constitute from 0.0001% to about 5.00% (w/v), but other amounts may be used as necessary for the application. In one embodiment, the preservative is benzalkonium chloride at a concentration of about 0.0001% to about 0.01% (w/v). In another embodiment, the preservative may be ethyl alcohol at a concentration of about 0.1% to about 1.5% (w/v).

In other embodiments, the hb-MSC composition may be further supplemented with additional anti-inflammatory agents, analgesics, antifungals, vitamins, sunscreens, agents for combating free radicals, sequestering agents, fragrances, fillers, natural products or extracts of natural products. The supplements may include organic small molecules, organometallic compounds, polymers, inorganic salts, proteins, growth factors, chemokines, DNA, RNA, or enzymes. In further embodiments the medium may be supplemented with sugars, proteins, insulin, signaling proteins, or any additional small molecules, including flavoring agents, or sweeteners. The supplements can also contain minor amounts of additives, such as substances that enhance isotonicity or chemical stability.

In one embodiment, preparing the hb-MSC composition involves dissolving or mixing the desired concentration of the antimicrobial agents and/or film-forming agents in an acceptable carrier. Additional ingredients, such as a buffering or pH adjusting agent, a preservative, a skin conditioning agent, a surfactant, a foaming agent, a viscosity-modifier, a colorant or opacifying agent, and/or a chelating agent may also be added. The solution is mixed as necessary, for example after one or more ingredients are added. The hb-MSC composition may include both solid and liquid ingredients. One of ordinary skill in the art will understand that certain ingredients may added to the mixing container at the same time, while other ingredients may be dissolved or mixed in a separate container, and then added to the solution along with the remaining ingredients. Although not required, it is recommended that the hb-MSC conditioned medium be added to the composition toward the end. The hb-MSC conditioned medium is prepared according to the methods disclosed above, and further described in the Examples below. It is also recommended to sample the solution prior to adding the stem cell conditioned medium, in order to check its pH and other indicators, so as to ensure that the combination will not negatively impact the stem cell conditioned medium, for example by denaturing the biological material in the medium as a result of a pH that is too high or too low. If necessary, the pH of the solution may be further adjusted by way of pH adjusting agent. After the stem cell conditioned medium is added, the solution is again mixed to form the composition. It should be understood that certain ingredients, for example a preservative and a surfactant, may be added to the stem cell conditioned medium prior to combining the medium with the solution containing the remaining ingredients. After mixing the ingredients, the viscosity, pH and other properties may be measured and further adjusted, if necessary.

The compositions disclosed herein may be used for a variety of purposes, including, but not limited to, any research, diagnostic, therapeutic or commercial purpose. Embodiments of the composition may also be used to treat a wide variety of other conditions, including, for example, burn treatment, skin care, angiogenesis, vasculogenesis, healing of organs or tissue, cosmetics, tissue inflammation, bacterial infections, wound applications, diabetes, pharmaceutical and ophthalmological applications, scar reductions, stimulating hair growth, in immunotherapy applications and for immunocorrection therapy, skin, bone marrow, or organ transplants, the treatment of organs or tissue, or for the treatment of other illnesses of humans or animals. As used herein, "treat" encompasses the cure of, remediation of, improvement of, lessening of the severity of, or reduction in the time course of, a disease, disorder or condition, or any parameter or symptom thereof. It should be understood that hb-MSCs, or hb-MSC conditioned medium, could be used for the same or similar purpose as the hb-MSC composition.

The hb-MSC composition may also be used for dermatological or cosmetic applications, in food supplements or animal feed supplements, for culturing cells, and in pharmaceutical applications. The hb-MSC composition may be used for preventative treatments, in response to an acute injury, or for the treatment of chronic injuries. In one embodiment, the hb-MSC composition may be used for the treatment of human illnesses or conditions. In another embodiment, the treatment may include veterinary applications.

In one embodiment, the hb-MSC composition may be advantageously used in the treatment of wounds, including acute and chronic wounds, broken bones, spinal cord injuries, gastric or diabetic ulcers, pancreas, liver, kidney, spleen, blood vessel injuries and other internal or external wounds as well as healing burns. For example, the hb-MSC composition may be used in topical applications to promote and/or accelerate wound healing, as described in Examples 7, 8, 10, and 11 and shown in FIGS. 4 and 5. In another embodiment, the hb-MSC composition could be used to treat wounds that would otherwise require surgical excision or drainage. For example, the hb-MSC composition may provide for increased perfusion of wound tissue.

The hb-MSC composition may be used in the cosmetic treatment of skin, including the treatment of wrinkles, frown lines, scarring, or to repair other skin conditions, such as those resulting from deleterious effects induced by UV light, and normal aging.

In one embodiment, the hb-MSC composition is used for treating or prophylactically against mastitis in cows. Using the hb-MSC composition may also lead to the repair or regeneration of post-mastitis structural damage of the mammary gland. In this embodiment, the method of using the hb-MSC composition includes, but is not limited to, topically applying the hb-MSC composition to the skin of the cow's teat (or udder) at pre-determined intervals, for example following each milking cycle. In a prophylactic regiment, the hb-MSC composition is applied to the entire herd, indefinitely. Of course, the hb-MSC composition may also be used (both prophylactically and as a mastitis treatment) for a predetermined period of time, followed by a period where the composition is not used. Embodiments of the composition may also be used as part of the regular course of mastitis treatment, including treatment with antibiotics. For example, one method of treating mastitis includes periodical use of an hb-MSC composition and, if the cow is infected or becomes infected with mastitis, also treating that cow with a course of antibiotics, as prescribed by a veterinary professional. The composition may have a synergistic effect when used with certain typical mastitis treatments. In another embodiment, the method of treating mastitis may include treatment of a cow with the hb-MSC composition without the use of antibiotics, thereby avoiding having to discard the milk as a result of the systemic presence of the antibiotics. In yet another embodiment, a method of treating mastitis includes the use of a first hb-MSC composition for treating cows that have been diagnosed with mastitis, and using a second hb-MSC composition for prophylactic purposes. For example, a second hb-MSC composition may be used for healthy cows or during the cow's dry period. It should be understood that the first and second compositions may be applied by different application methods. For example, the first hb-MSC composition may contain a film-forming agent and is applied topically, while the second hb-MSC composition does not contain a film-forming agent and is applied orally, or injected. In a different embodiment, the first and second hb-MSC compositions may be applied at the same time to the same animal, for example, an animal suffering from clinical mastitis. In a further embodiment, the method of treatment may include one or more steps, including a step of treating with an embodiment of an hb-MSC composition, and a second treatment with a conventional anti-mastitis treatment (such as an iodine-based teat dip).

In mastitis applications, the composition can be applied, for example, by way of a "dip-cup," a term the industry uses to refer to a container with an open top, filled with the composition, wherein the teats of the cow are dipped into the composition after the milking process is finished. The dip cup is designed to allow the animal's teat to fit into the open portion, but can also prevent the composition from spilling out. The composition may also be applied by spraying the animal's skin, for example using a spray bottle. It is not necessary to wipe the composition off the surface of the animal's skin after treatment and, if the composition includes a film-forming agent, the composition should not be wiped off until it is necessary to do so. Here, the term "apply" or "applied" shall be interpreted broadly. Thus, in addition to the above-disclosed methods of topical application, the composition may be topically applied by paint brushing, spreading, foaming, and other ways that are found acceptable in the dairy industry, such as by way of a wet wipe containing the composition. Topical shall also refer to compositions used as mouthwashes.

One of ordinary skill in the art will understand that delivery of the hb-MSC composition is not limited to topical applications; depending on the application, the composition may be delivered in any manner known in the art including, but not limited to an enteral route, including oral, buccal or sublingual, rectal, or by a parenteral route including intravenous, subcutaneous, intradermal, transdermal, intramuscular, intraperitoneal, via inhalation, intra-arterial, intrathecal, as an intramammary infusion, or topical application by a cutaneous, transdermal, nasal or ophthalmic route. As one of ordinary skill in the art would understand, the make-up of the composition may change based on the method of administration and the specific application. For example, if the composition is to be applied intravenously or intramuscularly, the composition should not include the film-forming agent. In an additional embodiment, the hb-MSC composition may be formulated for use in controlled, slow release vehicles.

It will be appreciated that the actual preferred amounts, modes of administration, and administration intervals of the hb-MSC composition in a specified case will vary according to the specific composition being utilized, the particular compositions formulated, the mode of application, the particular injury and subject being treated. Dosages of certain ingredients for each specific case can be determined using conventional considerations, e.g., by means of an appropriate conventional pharmacological protocol.

The hb-MSC composition may be used in any state. For example, the hb-MSC composition may take the form of tablets, capsules, skin patches, inhalers, eye drops, nose drops, ear drops, liquid washes, suppositories, lotions, creams, ointments, injectables, gels, hydrogels, foams, thin-films, powders, serums, salves, foundations, facial masks, lip care products, sunscreens, hair care products, such as shampoos, conditioners, including deep conditioners, hair care treatments, skin cleansers, exfoliants, compact formulations, or any other appropriate forms known to one of skill in the art.

In some embodiments, the hb-MSC composition may be used to coat sutures, medical equipment, or implantation devices. In another embodiment the hb-MSC composition may be combined with sutures, bandages, implants, stents, grafts, or in periodontal applications. The hb-MSC composition may also be used in wet wipes. The hb-MSC composition may also be added as wound filler or added to existing wound filling compositions to accelerate wound healing. In another embodiment, the hb-MSC composition may also be added to eye shadow, pancake makeup, compacts or other cosmetics.

In additional embodiments, liquid preparations of the hb-MSC composition may take the form of, for example, solutions, syrups or suspensions, or presented as a dry product for reconstitution with an acceptable carrier before use.

In another embodiment, the hb-MSC composition can be frozen for a set period of time. Alternatively, the hb-MSC composition can be lyophilized and frozen for a set period of time. Alternatively, the hb-MSC composition can be reconstituted as described above and frozen for a set period of time. Alternatively, the hb-MSC composition can be stored or kept at a temperature between room temperature (e.g., about 28° C.) and 0° C. The temperature range used is not intended to be exclusive, and one of skill in the art can envision alternative temperature ranges utilized depending on the nature of the application.

In another embodiment, the hb-MSC composition can be brought to room temperature before use. Alternatively, the hb-MSC composition can be applied at a temperature below room temperature. Alternatively, the hb-MSC composition can be utilized at a temperature above room temperature, as long as the temperature is not high enough to denature the biological material.

EXAMPLES

The following examples are included to demonstrate certain embodiments of the invention. Unless otherwise specified, the ingredient amounts are reported on the basis of w/v percent of the total composition. It should be appreciated by those of skill in the art that the techniques disclosed in the examples below represent techniques discovered by the inventors that may practice one or more embodiments of the invention. However, those of skill in the art should, in light of the present disclosure, appreciate that many changes can be made to the examples below without departing from the spirit and scope of the invention.

Example 1

Species Identification for hb-MSC Cells

PCR analysis was used to confirm that the cells are indeed from a rat. For PCR analysis COX-1 and VN1R1 genes were used for mitochondrial and nuclear DNA, respectively. Amplification of the COX-1 gene was carried out using multiplex-PCR, while amplification of the VN1R1 gene was carried out using standard PCR. Blood sample from a 38 yr old human male, a 32 yr old human female and a Wistar rat were used as control. The DNA was isolated from the cell culture utilizing a commercially available kit (PREP-GS-GENETICS, DNA Technology, Russia), according to the manufacturer instructions. All primers are commercially available, and were purchased from Evrogen, LLC.

The specific primers used for the PCR analysis were:

```
COX1-human:
                                      (SEQ ID NO: 1)
f'-TAGACATCGTACTACACGACACG
and (SEQ ID NO: 2)
r'-TCCAGGTTTATGGAGGGTTC.

COX1-rat:
                                      (SEQ ID NO: 3)
f'-CGGCCACCCAGAAGTGTACATC
and r'-GGCTCGGGTGTCTACATCTAGG.
                                      (SEQ ID NO:4)

VN1R1-human:
                                      (SEQ ID NO: 5)
f'-TGGTCTGGGCCAGTGGCTCC
and (SEQ ID NO: 6)
r'-GAGTGTTTTCCTTGTCCTGCAGGCA.
```

```
VN1R1-rat:
                                      (SEQ ID NO: 7)
f'-AGAAGAGTTACTGGCCCAAGGGACA
and (SEQ ID NO: 8)
r'-GGGGCTGAACGCTGGGAAGC.
```

Electrophoresis of the PCR products was carried out on 2% agarose gel utilizing a SubCellGT electrophoresis system (Bio-Rad). The gel was visualized using an ECX-F15.C (Vilber Lourmat) transilluminator. The electrophoretograms are shown in FIG. 3. Specifically, in FIG. 3, Lanes 1-5 show the COX1 gene base pairs. Lane 1 shows the result for control human DNA, while Lane 2 shows the result for control rat DNA. Lanes 3 and 4 show the results for hb-MSC samples. Lane 5 shows a negative control. Lanes 7-10 show the VN1R1 gene base pairs. Lane 10 shows a mixture of control human and control rat DNA. Lanes 9 and 7 show the results for hb-MSC samples. Lane 8 is the negative control. "M" signifies the DNA fragment marker lane. The electrophoresis confirms that the hb-MSCs were isolated from a rat and are not contaminated with material from human cells.

Example 2

Culture of rb-MSCs

Rat mesenchymal stem cells obtained under standard conditions were cultured and evaluated to show the differences between the unique isolated hb-MSC line and the typical rat mesenchymal stem cell (rb-MSCs).

Both the rb-MSC line and the hb-MSC line were isolated from primary cells collected from the bone marrow of Wistar rat tibias or femurs. Culturing of all cells took place under GMP conditions. In one embodiment, the procedure for obtaining the primary cells is as follows. The animals were anesthetized and euthanized. Under sterile conditions, both femurs and tibias from each rat were excised. Bone marrow was extruded by flushing with MEM-Earle medium supplemented with 15% fetal bovine serum (FBS). Marrow plug suspension was dispersed by pipetting, successively filtered through 70-μm mesh nylon filter, and centrifuged at 200 G for 10 min. The supernatant was discarded, and the cell pellet was re-suspended in the medium. The cells from one rat were seeded onto plastic flasks and incubated at 37° C. in a 5% $CO_2$ humidified atmosphere. On the third day, red blood cells and other non-adherent cells were removed and fresh supplemented medium was added to allow further growth. The adherent cells grown to 70% confluence were defined as the primary culture cells (p1).

To obtain the rb-MSC line, p1 rat mesenchymal cells were passaged according to standard conditions known in the art and in accordance with the manufacturer guidelines specified for RPMI-1640. The p1 cells were washed with $Ca^{2+}$-$Mg^{2+}$-free Hanks solution (Sigma, USA, H9394-500 ml) and detached by incubating with 0.25% trypsin-EDTA solution (Sigma, USA, T4424-100 ml) for 5-10 min at 37° C. Next, 5% FBS (Sigma, USA, F6765) supplemented Hanks solution was added to inactivate the trypsin. The cells were centrifuged at 200 G for 10 min, re-suspended in 1-2 ml RPMI-1640 media supplemented with 15% FBS, and counted manually using a hemocytometer grid with Neubauer ruling. The cells were then plated as p2 in 75 cm² flasks at densities of $1.0 \times 10^6$ cells/flask, using RPMI-1640 medium (Sigma, USA, R5886) supplemented with 15% FBS (Sigma, USA, F6765), 100 units/ml penicillin-100

μg/ml streptomycin (Sigma, USA, P4458), 100 ng/ml amphotericin (Sigma, USA, A2942), 2 mM L-Glutamine (Sigma, USA, G7513), 0.005 ml/ml vitamins (100×) for RPMI-1640 medium (Sigma, USA, R7256), and 0.005 ml/ml amino acids for RPMI-1640 medium (Sigma, USA, R7131). The flask, having a permeable sterile filter cap, was incubated at 37° C. in humidified incubator with a 5% $CO_2$ atmosphere. The RPMI-1640 medium (supplemented with 15% FBS) was replaced every 3 days over a 10- to 14-day period (or upon reaching 70% confluence). Following Passage No. 2 (p2) the cells were plated in 175 cm² flasks at densities of $2 \times 10^6$ cells/flask, and RPMI-1640 supplemented with 10% FBS was used. For each subsequent passage, the cells were plated similarly and grown to 70% confluence. Following 70% confluence the cells were split and re-seeded within a plastic culture flask. Passage 5 (p5) rb-MSCs were used as the comparison to the hb-MSC line.

Example 3

Culture of hb-MSC

To obtain the hb-MSC line, p1 rat mesenchymal cells were cultured according to the following method. First, the p1 cells were washed with $Ca^{2+}$-$Mg^{2+}$-free Hanks solution (Sigma, USA, H9394-500 ml) and detached by incubating with 0.25% trypsin-EDTA solution (Sigma, USA, T4424-100 ml) for 5-10 min at 37° C. Next, 5% FBS (Sigma, USA, F6765) supplemented Hanks solution was added to inactivate the trypsin. The cells were centrifuged at 200 G for 10 min, re-suspended in 1-2 ml RPMI-1640 media supplemented with 15% FBS, and counted manually using a hemocytometer grid with Neubauer ruling. The cells were then plated as p2 in 75 cm² flasks at densities of $1.0 \times 10^6$ cells/flask, using RPMI-1640 medium (Sigma, USA, R5886) supplemented with 15% FBS (Sigma, USA, F6765), 100 units/ml penicillin-100 μg/ml streptomycin (Sigma, USA, P4458), 100 ng/ml amphotericin (Sigma, USA, A2942), 2 mM L-Glutamine (Sigma, USA, G7513), 0.005 ml/ml vitamins (100×) for RPMI-1640 medium (Sigma, USA, R7256), and 0.005 ml/ml amino acids for RPMI-1640 medium (Sigma, USA, R7131). The flask, having a permeable sterile filter cap, was incubated at 37° C. in humidified incubator with a 5% $CO_2$ atmosphere. The RPMI-1640 medium supplemented with 15% FBS was replaced every 3 days over a 10- to 14-day period (or upon reaching 70% confluence).

Following Passage No. 2 (p2) the cells were plated in 175 cm² flasks at densities of $2 \times 10^6$ cells/flask, and RPMI-1640 supplemented with 10% FBS was used. The cultures continued to be grown at 37° C. in humidified incubator with a 5% $CO_2$ atmosphere. Following the third Passage (p3), the cells were passaged at a reduced $CO_2$ concentration. To reduce the $CO_2$ concentration, the culture flask was sealed with an impermeable cap under atmospheric $CO_2$ conditions and incubated at 37° C. No supplemental $CO_2$ was used in all of the following passages. As previously described, fresh RPMI-1640 medium supplemented with 10% FBS was added and replaced every 3 or 4 days for about 14 days. For each passage, the cells were plated similarly and grown to 70% confluence. Following 70% confluence the cells were split and re-seeded within a plastic culture flask. Passage 9 (p9) hb-MSCs were compared with rb-MSCs. PCR analysis (Nanodiagostika, LLC, RUS) confirmed that the hb-MSCs are free of contamination by bacteria, viruses, mycoplasma, or fungi.

The hb-MSC line was preserved utilizing 10% DMSO and 50% FBS medium at liquid nitrogen temperatures with a concentration between $3.0 \times 10^6$ to $5.0 \times 10^6$ cells in a 2 milliliter (ml) ampoule.

Example 4

Flow Cytometry Characterization of hb-MSCs

A flow cytometry experiment was carried out to identify the cell surface markers of the hb-MSC and rb-MSC lines. For purpose of this experiment, 50 μl of the corresponding antibody was added to a 100 μl cell suspension. The suspension was vortexed for a period of five seconds (BioVortexV1, BioSan) and maintained at +4° C. for a period of 30 minutes in absence of light. Following incubation, the mixture was diluted with 500 μl of saline solution and washed twice via centrifugation to remove excess reagents. Each centrifugation was carried out at 400 G for a period of 10 minutes (ELMI). In each sample at least 10,000 counts were analyzed. The results were analyzed using WinMDI 2.7 analysis program and are shown in FIG. 1. A summary of the surface markers expressed by the rb-MSC and the hb-MSC lines is provided in Table 1 below.

TABLE 1

| rb-MSC and hb-MSC line surface markers | | |
|---|---|---|
| Cell Surface Marker | hb-MSC line | rb-MSC line |
| CD29 | 95.0% | 94.6% |
| CD44 | 94.8% | 98.7% |
| CD11b | <3% | <3% |
| CD45 | <3% | <3% |

Typical bone marrow rat mesenchymal cells exhibit positive expression of CD44, CD29 markers and negative expression of CD45, and CD11b markers. As shown in Table 1 above, the hb-MSC line exhibits surface markers consistent with that of a bone marrow mesenchymal stem cell of a rat. This demonstrates that the method of obtaining hb-MSCs does not result in a change to the surface markers of the cells.

Example 5

Analysis of Culture Media Conditioned by the rb-MSC and hb-MSC Cell Lines

To compare the impact of the hb-MSCs and rb-MSCs on the culture medium nine (9) separate 75 cm² flasks of each cell line were plated at a density of $0.7 \times 10^6$ cells/flask. The cells were passaged in RPMI-1640/10% FBS supplemented with 5% $CO_2$ in an incubator set to 37° C. The cell flasks were closed with a gas-permeable cap. A total of 9 time periods were analyzed: 24, 48, 96, 144, 192, 216, 240, 264, and 288 hours. A single flask of cells was analyzed at each prescribed time period. The media was exchanged in all remaining vials following three days (72 hours), five days (120 hours), seven days (168 hours), and daily thereafter. Lactate concentration and pH of the medium was measured at each of the nine periods. With the exception of the 48 hour measurement, the periods were selected so that measurement would take place 24 hours after the media was exchanged. Lactate was measured utilizing a biochemical analyzer, in triplicate, with a lactate characterization kit from SPINREACT. pH was measured using an electronic pH meter (METTLER TOLEDO InLab Versatile Pro). Cell count was also measured at each of the periods, and the cells underwent at least one population doubling at a pH below 7.05.

Figure 6:
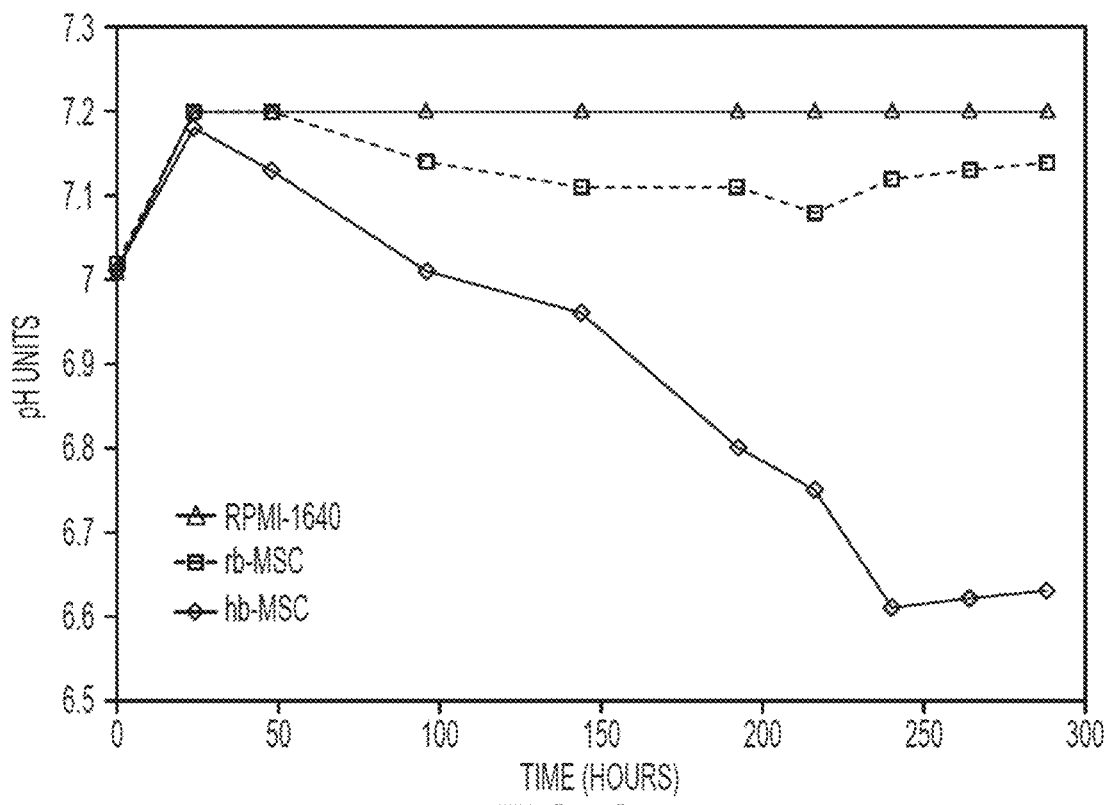
FIG. 6 illustrates the change in pH over time for RPMI-1640 media, rb-MSC conditioned media, and hb-MSC conditioned media.
Figure 7:
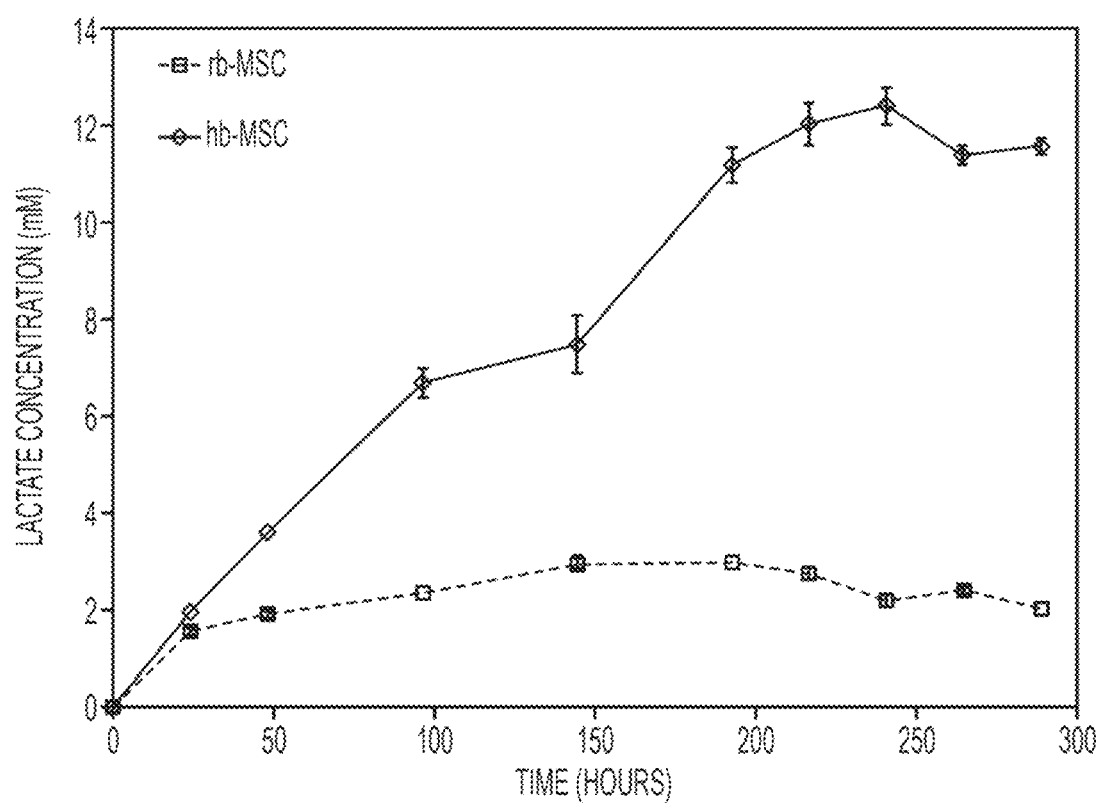
FIG. 7 illustrates the change in the lactate concentration (mM) during cell culture for hb-MSCs and rb-MSCs.

FIG. 6 illustrates the change in pH over time for pure RPMI-1640 culture media, rb-MSC conditioned media, and hb-MSC conditioned media measured at the times of cell collection described in this Example. FIG. 7 shows the change in the lactate concentration (mM) for rb-MSC and hb-MSC lines during culture. The error bars represent one standard deviation in lactate concentration. The following table, which is based on the data in FIGS. 6 and 7, shows a comparison of the various measurements for rb-MSCs and hb-MSCs in this Example.

TABLE 2

Methods of differentiation for hb-MSC and rb-MSC lines

| Method of Differentiation | rb-MSCs | hb-MSCs |
|---|---|---|
| pH of media following at least 150 hours in culture (within 24 hours of media exchange) | >7.05 (at all times) | <7.0 |
| Maximum deviation from pH of RPMI-1640 media (within 24 hours of media exchange) | <0.15 | >0.4 |
| Lactate concentration of media following at least 96 hours in culture (within 24 hours of media exchange) | <3 mM | >4 mM |
| Number of population doublings at a pH below 7.05 | 0 | >1 |

Example 6

Comparison of Factors in Media Conditioned by rb-MSC and hb-MSC Cell Lines

The rb-MSC and hb-MSC lines may be distinguished by comparing the factors produced by each line when the line is maintained in culture media. To compare the factors produced by the hb-MSCs and rb-MSCs, seven (7) separate 75 cm$^2$ flasks of each cell line were plated at a density of 0.7×10$^6$ cells/flask. The cells were passaged in RPMI-1640/ 10% FBS supplemented with 5% $CO_2$ in an incubator set to 37° C. It will be understood by one of ordinary skill in the art that the addition of supplemental sera will impact the starting concentration of factors in the media prior to being conditioned. The cell flasks were closed with a gas-permeable cap. A total of 7 time periods were analyzed: 96, 144, 192, 216, 240, 264, and 288 hours. A single flask of cells was analyzed at each prescribed time period. The media was exchanged in all remaining vials following three days (72 hours), five days (120 hours), seven days (168 hours), and daily thereafter. The periods were selected so that measurement would take place 24 hours after the media was exchanged. Factor analysis was carried out using Eve Technologies Rat Cytokine Array/Chemokine Array 27-Plex Panel, TGF-Beta 3-Plex Cytokine Array and Rat Bone 1-Plex Array. The specific factors compared in Table 3 include interleukin-10 (IL-10), interferon gamma-induced protein 10 (IP-10), CXCL1 (GRO/KC), vascular endothelial growth factor (VEGF), osteoprotegerin (OPG), transforming growth factor beta 1 (TGF-β1), transforming growth factor beta 2 (TGF-β2), and transforming growth factor beta 3 (TGF-β3). It should be understood that multiplex measurements depend on a calibration curve and specific antibody use and thus could vary to some degree, as understood by one of ordinary skill in the art.

The range of factors observed during the analyzed time periods is summarized in Table 3 below. It should be understood that concentration of factors may depend on the time period that the cells are cultured and number of cells in the flask.

TABLE 3

Comparison of factor concentrations for rb-MSCs and hb-MSCs in pg/ml

| Factor | rb-MSC | hb-MSC |
|---|---|---|
| IL-10 | 0 to 12 | 12 to 38 |
| IP-10 | 7 to 26 | 18 to 120 |
| GRO/KC | 14 to 100 | 460 to 5600 |
| VEGF | 300 to 2400 | 760 to 15800 |
| OPG | 540 to 3200 | 0 to 90 |
| TGF-β1 | 550 to 2600 | 67 to 2000 |
| TGF-β2 | 520 to 3200 | 170 to 2900 |
| TGF-β3 | 100 to 610 | 0 to 40 |

Comparative Analysis of rb-MSC and hb-MSC Lines

There are a number of ways to distinguish the hb-MSC line from the rb-MSC line. One way to distinguish two lines is by measuring the pH of the culture media during cell growth. Example 5 describes measuring the pH of culture media (RPMI-1640) conditioned by the rb-MSC and hb-MSC lines over a period of 288 hours. Prior to culture, the pH of RPMI-1640 was measured as approximately 7.01. As expected, the prescribed amount of supplemental $CO_2$ for RPMI-1640 (i.e. 5%) effectively buffered the pH of the control RPMI-1640 to 7.2 for the entire duration of the experiment. The pH of the rb-MSC culture remained between approximately 7.08 and 7.2 throughout the duration of the entire experiment. For hb-MSCs, however, the pH decreased from approximately 7.2 at 24 hours to a pH of approximately 6.6 over the course of the following 216 hours and remained at a pH approximately 6.6 for the duration of the experiment. Following 150 hours in culture, the pH of the culture medium decreases to below 7.0 within 24 hours of media exchange. Similarly, following 150 hours in culture, the pH of the culture medium decreases by at least 0.4 units from the pH of RPMI-1640 within 24 hours of media exchange. The difference in the pH of media conditioned by the rb-MSC and hb-MSC lines demonstrates that the two lines are different.

Another method to distinguish the hb-MSC line from the rb-MSC line is by measuring the production of lactate by the cells in the medium, as described in Example 5. FIG. 7 shows that hb-MSCs produce lactate resulting in a concentration that exceeds that produced by rb-MSCs. Following about 96 hours in culture, the hb-MSCs produce at least 4 mM of lactate within 24 hours of media exchange, and can produce as much as 12.4 mM of lactate within 24 hours of media exchange. By contrast, the concentration of lactate produced by rb-MSCs never exceeds 3 mM within 24 hours of media exchange. The difference in the lactate concentration in media conditioned by the rb-MSC and hb-MSC lines demonstrates that the two lines are different.

Another method to distinguish the hb-MSC line from the rb-MSC line is by evaluating the media conditioned by each line. For purposes of this comparison, the media was collected as described in Example 6. The results of the factor measurements are summarized in Table 3 above. The diftioned by rb-MSCs and media conditioned by hb-MSCs demonstrates that the two lines are different.

In total, the characterization methods described above lead to the conclusion that the hb-MSC line is different from the rb-MSC line.

Example 7

Morphometric Study of Wound Closure

Figure 4:
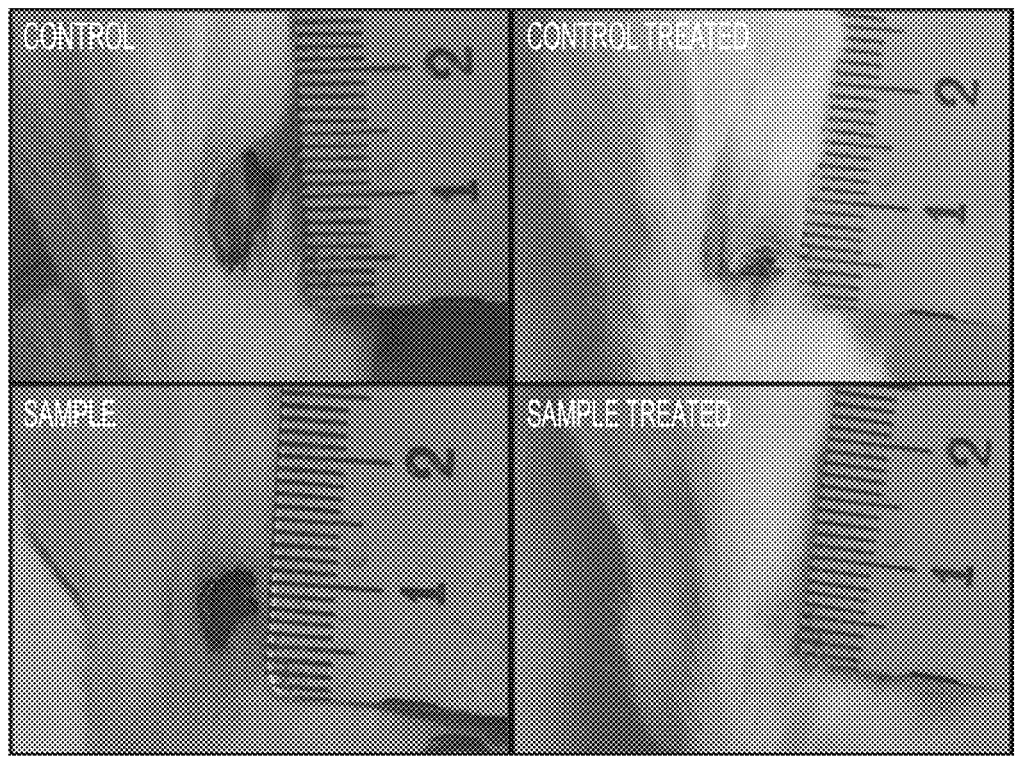
FIG. 4 shows a comparison of mouse wounds nine days after being treated by RPMI-1640 culture medium and by the hb-MSC composition.
Figure 5:
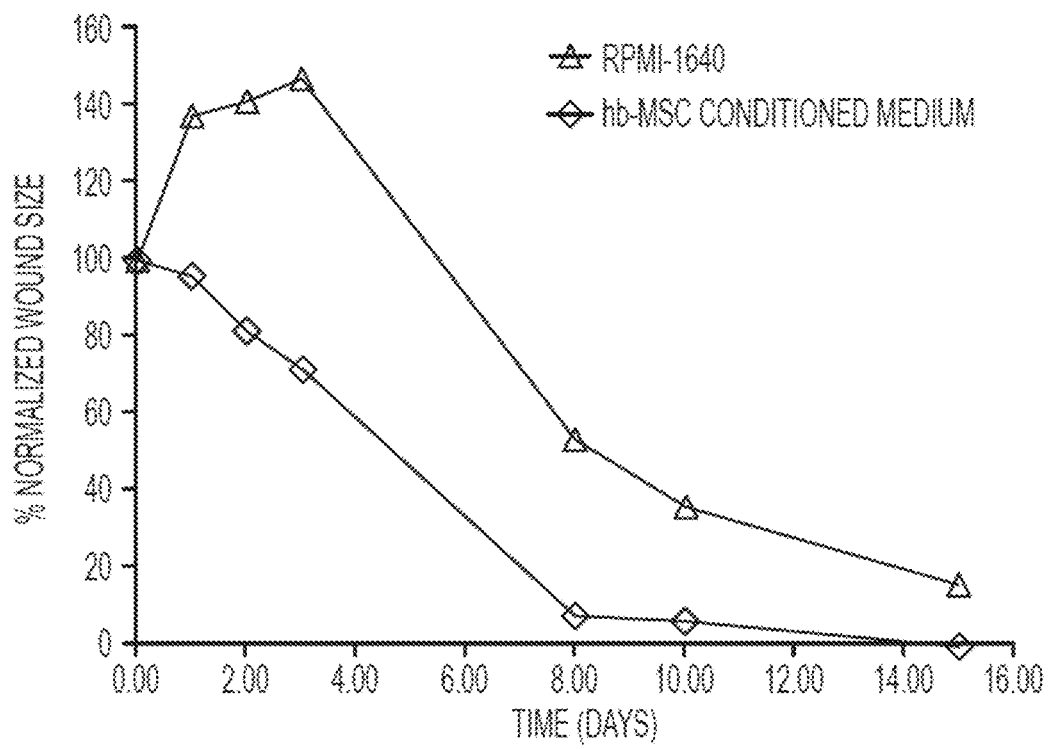
FIG. 5 shows the relative speed of wound closure for mouse wounds treated by RPMI-1640 culture medium and by the hb-MSC composition.

A morphometric study was undertaken to follow the wound healing process of laboratory mice. All animal experiments were carried out in the veterinary surgery department of Moscow State Academy of Veterinary Medicine and Biotechnology named after K. I. Scriabin. White laboratory mice 3 to 5 months in age weighing approximately 22-25 grams were used for all experiments. A total of six mice were used in each experiment. An incision of approximately 0.5 cm in diameter was made in a freshly shaved shoulder blade area of each anesthetized animal. Following the incision, the animals were sorted into control and sample groups, with three mice per group. Each wound was photographed to obtain digital morphometric parameters. Thirty minutes following the incision each wound was treated with a 50 µl drop of either RPMI-1640 or the hb-MSC composition. In this example, the hb-MSC composition included the hb-MSC conditioned medium as described in Example 6, wherein the conditioned medium collected at each of the different conditioning time periods (96, 144, 192, 216, 240, 264, and 288 hours) was combined in a single container. The composition also included benzalkonium chloride as a preservative, and Triton X-100 as a surfactant. The wound size was measured once each day for a period of 15 days. The hb-MSC composition and RPMI-1640 were applied to each animal in the respective groups once per day following wound assessment. The digital images showing the comparative healing process of wounds treated with the hb-MSC composition and the RPMI-1640 medium are shown in FIG. 4. FIG. 4 shows a mouse from the control group (treated with RPMI-1640) on day 1 of treatment and the same mouse on day 9 of treatment. FIG. 4 also shows a mouse from the sample group (treated with the hb-MSC composition) on day 1 of treatment and the same mouse on day 9 of treatment. The effect of the treatment on average wound size using the hb-MSC composition vs. RPMI-1640 is illustrated in FIG. 5.

Example 8

Morphometric Study of Mastitis Bacteria-Contaminated Wound Closure

A bacteria-contaminated mouse wound model was used to evaluate the efficacy of several different hb-MSC compositions. The mouse wound model of this experiment is similar to the model described in connection with Example 7, but with two differences. First, in the present example, a mixture of bacterial pathogens was added to the mouse's wound to slow down the wound's natural healing process. The mixture was developed through experimental trials, such that the application of the bacterial mixture to the wound resulted in a consistent multi-day healing period (negative control). The second difference is the method of incision used for the present experiment. Specifically, a punch biopsy of approximately 0.6 cm in diameter (Epitheasy, Italy) was taken in a freshly shaved shoulder blade area of each anesthetized animal. Use of the punch biopsy improved the accuracy and consistency in the wound size and depth, as the punch biopsy results in a full thickness wound, consistently and cleanly removing the epidermis and dermis layers, while leaving the muscle tissue intact.

All animal experiments were carried out in the veterinary surgery department of Moscow State Academy of Veterinary Medicine and Biotechnology named after K. I. Scriabin. White laboratory mice 3 to 5 months in age weighing approximately 22-25 grams were used for all experiments. The testing was performed as follows. Following the biopsy, the animals were sorted into control and sample groups, with at least five mice per group. In some cases more than five mice per group were used. Each wound was photographed to obtain the initial morphometric parameters. After obtaining the morphometric parameters of the wound, a 50 µl drop of the bacterial pathogen cocktail was applied to the wound. The mixture of pathogens in the cocktail included mastitis-causing bacterial strains. The concentrations of the bacterial pathogens in the cocktail were chosen based on a series of experiments designed to produce a consistent wound healing period. Thirty minutes following bacterial contamination each wound was treated with a 50 µl drop of one of the test compositions. The test compositions were applied to each animal in the respective groups once per day following wound assessment. Digital images of the wound were taken on the first, second, and fourth days following the biopsy.

Table 4 shows several exemplary compositions used for this experiment, with the values presented on a weight percent basis. Table 5 shows the VEGF and GRO/KC concentrations for each of the compositions of Table 4, with the other factors being proportional as generally indicated in Table 3. It is understood that these compositions are provided as examples only and nothing therein should be taken as a limitation upon the overall scope of the invention. Three and five layer flasks with total growth areas of 500 cm$^2$ and 870 cm$^2$, respectively, were used to form the hb-MSC conditioned media for this experiment. The starting cell seed density was about 2.1×10$^6$ cells/flask for both the three-layer (Compositions #5-10) and the five-layer flask (Composition #4). After obtaining the conditioned media, the compositions were formed by combining the listed ingredients (except the hb-MSC conditioned media) in an aqueous excipient and mixing them for a period of time sufficient to ensure complete dissolution. The concentrated solution was then sampled in order to check its pH and other indicators, so as to ensure that the combination will not negatively impact the stem cell conditioned medium. Next, hb-MSC conditioned media was added to the concentrated solution of pre-dissolved ingredients and the combined solution was again mixed to form the specified compositions.

TABLE 4

| | Compositions used in Example 8 | | | | | | | | | |
|---|---|---|---|---|---|---|---|---|---|---|
| Ingredient | 1 | 2 | 3 | 4 | 5 | 6 | 7 | 8 | 9 | 10 |
| Aqueous excipient | ✓ | ✓ | ✓ | ✓ | ✓ | ✓ | ✓ | ✓ | ✓ | ✓ |
| Conditioned media | x | x | x | ✓ | ✓ | ✓ | ✓ | ✓ | ✓ | ✓ |

TABLE 4-continued

Compositions used in Example 8

| Ingredient | 1 | 2 | 3 | 4 | 5 | 6 | 7 | 8 | 9 | 10 |
|---|---|---|---|---|---|---|---|---|---|---|
| Nisin | x | x | 5E-3 | x | x | x | 5E-3 | x | 5E-3 | x |
| Amoxicillin | x | x | x | x | x | x | x | 0.1 | x | x |
| Methocel | x | 5E-1 | x | x | x | 5E-1 | x | x | 5E-1 | x |
| Benzalkonium Chloride | x | x | x | 5E-4 | 5E-4 | 5E-4 | 5E-4 | 5E-4 | 5E-4 | 5E-4 |
| Triton X-100 | x | x | x | 5E-2 | 5E-2 | 5E-2 | 5E-2 | 5E-2 | 5E-2 | 5E-2 |
| Glycerin | x | x | x | x | x | x | x | x | 5 | 5 |

TABLE 5

VEGF and GRO/KC Concentrations used in hb-MSC Compositions

| Composition # | VEGF (pg/ml) | GRO/KC (pg/ml) |
|---|---|---|
| 4 | 300-500 | 40-60 |
| 5-10 | 1500-3000 | 150-300 |

The impact of the above-described compositions on the wound healing process was evaluated in two ways: (1) through a clinical evaluation of the wound healing process; and (2) through a morphometric method using digital image analysis software (ImageJ). For each mouse, portions of the wound that exhibited bleeding, purulent exudate, lack of epithelial layer formation or lack of scabbing were considered to be in the process of healing. Portions of the wound that exhibited wound contraction, granulation tissue covered with a flat, light and even epithelial layer or scab were considered as healed.

The wound-healing rate was expressed as a percent of injured tissue based on the original measured wound size, as shown in Table 6 below.

TABLE 6

Bacteria-Contaminated Wound Model Results

| Composition # | Day 0 (% wound size) | Day 1 | Day 2 | Day 4 |
|---|---|---|---|---|
| 1 | 100 | 80 | 74 | 60 |
| 2 | 100 | 66 | 41 | 31 |
| 3 | 100 | 42 | 28 | 19 |
| 4 | 100 | 41 | 22 | 9 |
| 5 | 100 | 33 | 26 | 10 |
| 6 | 100 | 20 | 14 | 7 |
| 7 | 100 | 33 | 13 | 5 |
| 8 | 100 | 34 | 15 | 6 |
| 9 | 100 | 20 | 10 | 6 |
| 10 | 100 | N/A | 25 | 12 |

Specifically, Table 6 shows that the addition of the individual components to the aqueous excipient does not provide a similar wound healing impact as the compositions containing stem cell conditioned media. It is also shown that the efficacy of the stem cell conditioned media did not diminish with the addition of either the antimicrobial or film-forming agents; rather, the results show a synergistic effect resulting from the combination. For example, the results demonstrate that, when the composition includes stem cell conditioned media and a film-forming agent, the composition demonstrates an unexpected "controlled release" delivery to the targeted area of application and exhibits an improved healing speed. Likewise, by including an antimicrobial agent in the composition, the composition can improve both its immediate and prolonged wound healing effect. The results also show that the compositions used in this example are stable, and that the addition of the listed ingredients did not reduce (and in some cases improved) the efficacy of the composition.

Example 9

Evaluation of Film Forming Properties

An experiment was conducted to test the film forming properties of a composition containing a film-forming agent, in this case methyl cellulose. Four different w/v percent concentrations of methyl cellulose (Methocel, The Dow Chemical Company, 40-100) were used in the study, as shown in Table 7 below.

TABLE 7

Results of Film Forming Experiment

| Composition # | Conditioned stem cell media | Methyl Cellulose | Glycerin | Dye (yes/no) | Film formation (yes/no) |
|---|---|---|---|---|---|
| A | Yes | 0.25% | Yes | Yes | Yes |
| B | Yes | 0.5% | Yes | Yes | Yes |
| C | Yes | 1.0% | Yes | Yes | Yes |
| D | Yes | 1.5% | Yes | Yes | Yes |

The compositions used in this experiment were prepared by adding methyl cellulose, glycerin, and a red dye (F&DC 40) to a continuously stirred aqueous excipient, and stirring until the methyl cellulose was completely dissolved. The pH of the mixture was then evaluated to ensure the compatibility with the conditioned stem cell medium. The conditioned stem cell medium was then added to the concentrated pre-composition and stirred. The composition used glycerin as a conditioning agent and the red dye (F&DC 40) was included to enhance the contrast of the formed film. Following complete dissolution of the methyl cellulose, a 15 ml centrifuge tube (SPL Life Sciences) was dipped into the composition for a period of 10 seconds. The tube was removed from the composition, allowed to dry, and was subsequently assessed for film formation quality. All four evaluated compositions resulted in the formation of a film on the surface of the centrifuge tube, demonstrating that the incorporation of stem cell conditioned media did not negatively affect the properties of the film-forming agent. Additionally, the same experiment was carried in vivo, by applying the same composition to the teats of a cow using a teat dip cup. The stem cell media composition containing a specified amount of the film-forming agent was poured into a teat dip cup (NASCO). The teat dip cup was used to apply approximately 0.75 ml to each individual teat. The liquid was allowed to dry, was subsequently photographed and assessed for film formation quality. The in vivo experiment confirmed the results of the centrifuge tube experiment.

Example 10

Mastitis Treatment

The efficacy of stem cell conditioned media for treating clinical and subclinical mastitis was evaluated in field trials over a period of three months. The field trials took place at a dairy farm outside of Moscow, Russia. A total of about 600 cows were evaluated during the experiment. All cows were kept on the same diet, and milked using the same milking methods. The cows were split into two groups: a control group of about 400 cows (located in a one portion of the farm), and a treatment group of about 200 cows (located in a second, separate, portion of the farm).

Cows in the control group were treated according to the current best-practices for mastitis management already employed at the dairy farm, which included post-milking treatments with an iodine-based teat dip, up to three times per day. Cows in the treatment group were treated the same way as the control group, except that a stem cell conditioned media composition was used instead of the iodine-based teat dip. In the treatment group, each cow was treated with the stem cell conditioned media composition after each milking, up to three times per day. The stem cell conditioned media composition used in this experiment corresponds to Composition #5 in Example 8. In both the control and the treatment groups, the application of the iodine-based teat dip and the stem cell conditioned medium composition was carried out by way of a standard teat dip cup.

Each group was milked into a separate bulk tank for collection purposes. The total number of clinical and subclinical cases was recorded for each group, as well as for each individual cow within the groups. Clinical mastitis was diagnosed by a licensed veterinarian. Subclinical mastitis was diagnosed using a digital mastitis meter (DRAMINSKY) operated by a licensed veterinarian. Additionally, bulk tank somatic cell counts were recorded throughout the experiment for each separate group using a viscometric somatic cell analyzer (COMATOC-B). It should be noted that cows exhibiting clinical mastitis symptoms were not milked into the bulk tank in either the control or treatment groups. The groups were also analyzed for a period of one week prior to starting treatment in order to set a baseline pre-treatment level of mastitis and pre-treatment level of bulk tank somatic cell counts for each group.

The results of the field trials are presented in Table 8, and include: (1) rate of mastitis incidence in cows defined as healthy (i.e., cows that did not have clinical or subclinical mastitis) at the onset of the experiment; and 2) bulk tank somatic cell count for the control and treatment groups.

TABLE 8

Mastitis Treatment Results

| Group | % healthy cows | | Somatic cell count | | |
|---|---|---|---|---|---|
| | start | finish | prior to treatment | finish | average |
| Control | 100% | 53% | 500 | 400 | 390 |
| Treatment | 100% | 84% | 600 | 200 | 230 |

As shown in Table 8, the incidence of clinical or subclinical mastitis in the treatment group was 31% lower than in the control group. This demonstrates that treatment with the conditioned media results in a prophylactic effect against mastitis occurrence. The somatic cell counts in the bulk tank decreased by 50% at the finish of the experiment. Additionally, the average somatic cell count over the three month experimental period was 41% lower relative to the control group. The results demonstrate that treatment with the conditioned media composition was effective in treating mastitis and exhibited a prophylactic effect. Following the experiment, the beneficial effects of the composition continued for a period of at least two weeks, and in some cases longer.

Example 11

Therapeutic Effect of the hb-MSC Composition

In order to test the therapeutic effect of the hb-MSC composition, experiment were conducted on a variety of animals, including canines (65+), felines (80+), equines (40+), livestock (25+), rodents (200+), and ayes (15+). The hb-MSC composition was used to treat a wide variety of conditions in the above test subjects. The hb-MSC composition used in this example was the same as in Example 7. These treatments included: 1) wound applications, including post-operative incision sites; 2) burn treatments, including chemical burns; 3) ulcers including diabetic ulcers; 4) fistulas, 5) tissue inflammation or bacterial infections, including purulent inflammations, conjunctivitis, keratitis, mastitis, phlegmon, gastritis, and dermatitis; 6) orthopedic applications, including bone fractures; and 7) treatment of varying tissues including skin, ligaments, and muscle tissue. In the experiments, the hb-MSC composition was delivered by the following methods: topical, oral, nasal, intravenous, subcutaneous, intradermal, transdermal, intramuscular and intraperitoneal. Additionally, the hb-MSC composition was applied utilizing sterile napkins, as an aerosol, and by direct application to the affected area (including by using teat dip cups). The hb-MSC composition was effective in treating all of the above conditions, showing improved regenerative effects, wound closure speed, significant reduction of inflammation and local bacterial colonization, antimicrobial effects, angiogenesis and vasculogenesis, reduced scarring of tissue and a restoration of hair follicles in the affected area. The substantial regenerative effects observed in these experiments were consistent with the results of the mouse wound experiments described in Example 7. In all cases, the animals remained healthy after treatment with the hb-MSC composition. For all cases, toxicity, irritation, sensitization and bio-accumulation were assessed. All tracked indicators for all animals within 30 days of administration of the hb-MSC composition remained within the normal range as assessed by blood tests. Histology of the kidneys liver, lungs, spleen, intestines, and soft tissues did not demonstrate any signs of acute or chronic toxicity from the application of the hb-MSC composition. There also were no recorded instances of allergic reactions, infections, or other negative side effects. Taken together, these experiments demonstrate that the hb-MSC composition may be used to safely and effectively treat a wide variety of conditions in humans and animals, including burn treatment, skin care, angiogenesis, vasculogenesis, healing of organs or tissue, cosmetics, tissue inflammation, bacterial infections, wound applications, diabetes, pharmaceutical and ophthalmological applications, scar reductions, stimulating hair growth, in immunotherapy applications and for immunocorrection therapy, skin, bone marrow, or organ transplants, the treatment of organs or tissue, or for the treatment of other illnesses.

Example 12

Thermal Stability

A repeated temperature cycling experiment was conducted in order to test the thermal stability of a composition containing stem cell conditioned media. Specifically, Composition #9 from Example 8 was evaluated in this experiment. The temperature range during the experiment was cycled between +4-8° C. and +20-25° C. The thermal cycling was carried out by placing the composition into a refrigerator held at +4-8° C. for a period of 23 hours followed by the removal of the composition to equilibrate at +20-25° C. for a period of one hour. Following temperature equilibration, the composition was visually inspected for the presence of any precipitate or for any change in the composition appearance. The composition was subsequently returned to the refrigerator for the next cooling period and the cycle repeated for 11 days. The result of the experiment is outlined in Table 9, below. From the results of the experiment it is concluded that the composition is stable upon thermal cycling.

TABLE 9

Thermal Stability Results

| Day | Time at +20° C. | Precipitate or visual change? |
|---|---|---|
| 1 | 1 hour | No change observed |
| 4 | 1 hour | No change observed |
| 5 | 1 hour | No change observed |
| 6 | 1 hour | No change observed |
| 7 | 1 hour | No change observed |
| 8 | 1 hour | No change observed |
| 11 | 1 hour | No change observed |

Example 13

Broad Spectrum Stability

An experiment was conducted to evaluate the stability of a composition containing conditioned media formulated with a number of different additives. The stability was evaluated in two ways: (1) based on both a visual inspection (to check for precipitation); and (2) by an ELISA assay, to check for VEGF concentration. In total, 14 compositions, as well as the control conditioned stem cell media were evaluated by this method. Each tested composition was formulated by adding specified volume or weight of a commercial pharmaceutical product (identified in Table 10) to a 10 ml volume of conditioned stem cell media. Once the ingredients were combined, the composition was stirred until the ingredients were completely dissolved. In all cases, the conditioned stem cell media included 0.0005% of benzalkonium chloride and 0.05% of Triton X-100. The compositions were stored for a period of 48 hours at a temperature of +4-8° C., prior to being evaluated for their stability, and were visually examined again at 168 hours.

TABLE 10

Compositions of Example 13

| # | Commercial Pharmaceutical | Amount Added |
|---|---|---|
| 1 | Control | None |
| 2 | Nisin | 0.5 mg |
| 3 | Methocel | 50 mg |
| 4 | Glycerin | 500 mg |
| 5 | Malavit | 0.05 ml |
| 6 | Dexamethasone | 1 ml |
| 7 | Aevit | 100 ml |
| 8 | Phenazone + Lidocaine | 0.25 ml |
| 9 | Fenistil | 1 ml |
| 10 | Aspirin | 10 mg |
| 11 | Camphor Oil | 0.5 ml |
| 12 | Amoxicillin | 12.5 mg |
| 13 | Panthenol | 1 ml |
| 14 | Ethyl Alcohol | 0.07 ml |
| 15 | Hyaluronic acid | 0.5 ml |

In each case, there was no precipitate observed in the composition. Additionally, in all cases, the amount of VEGF did not materially decrease (more than 10%) as compared to the amount of VEGF in the control conditioned media. Thus, the results show that, in all cases, the composition remained stable, and the addition of the commercial pharmaceutical products did not result in a negative effect on the conditioned stem cell media.

While the present invention has been particularly shown and described with reference to examples of embodiments thereof, this application is intended to cover any departures from the present disclosure as come within the known or customary practice in the art to which this invention pertains and it will be understood by those of ordinary skill in the art that various changes in form and details may be made therein without departing from the spirit and scope of the present invention as defined by the following claims and their equivalents.

What is claimed is:

1. A cell-free composition comprising:
a mesenchymal stem cell conditioned medium, wherein the conditioned medium contains VEGF at a concentration of at least 760 pg/ml, TGF-β1 at a concentration of at least 67 pg/ml, TGF-β2 at a concentration of at least 170 pg/ml, and osteoprotegerin (OPG) at a concentration of less than 250 pg/ml.

2. The composition of claim 1, wherein the conditioned medium further contains at least 460 pg/ml of GRO/KC, and at least 18 pg/ml of IP-10.

3. The composition of claim 1, wherein the mesenchymal stem cells are obtained from bone marrow, and wherein the conditioned medium further contains osteoprotegerin (OPG) at a concentration of less than 90 pg/ml.

4. The composition of claim 1, wherein the conditioned medium is conditioned by mesenchymal stem cells having at least one of the following characteristics when $0.7 \times 10^6$ of the cells are seeded into a 75 cm$^2$ flask and cultured for at least 96 hours: (a) the cells produce at least 4.5 mM of lactate within 24 hours of media exchange; and (b) the cells produce at least 150 pg/ml of GRO/KC within 24 hours of media exchange.

5. The composition of claim 1, wherein the composition further comprises one or more rheology modifier present at a concentration ranging from 0.01% to 2% (w/v), and wherein the rheology modifier is at least one member selected from the group consisting of a cellulose derivative, polyvinyl pyrrolidone, acrylate polymer, polyvinyl alcohol (PVA), silicone, latex, gum, starch, arabinoxylan, glucomannane, glycerin, and sodium alginate, or mixtures thereof.

6. The composition of claim 1, wherein the composition further comprises one or more antimicrobial agent present at a concentration ranging from 0.001% to 1.0% (w/v), wherein the antimicrobial agent is at least one member selected from the group consisting of an aminoglycoside, tetracycline, β-lactam, peptide based antibiotic, glycopeptide antibiotic, Lantibiotic, polymyxin, colicin, microcin, and fluoroquinolone, or mixtures thereof.

7. The composition of claim 1, wherein the composition further comprises at least one member selected from the group consisting of a buffering agent, pH adjusting agent, a preservative, a surfactant, a foaming agent, a colorant, one or more acceptable carrier, and a chelating agent.

8. The composition of claim 1, wherein the composition further comprises one or more conditioning agent present at a concentration ranging from 0.1 to 30% (w/v), and wherein the conditioning agent is at least one member selected from the group consisting of glycerin, propylene glycol, polyethylene glycol, fatty alcohol, mineral oil, petroleum jelly, sorbitol, lactylate, D-Panthenol, Hyaluronic acid, Polyquaternium-7, Stearic Acid, Silk amino acid, Aloe Vera, shea butter, and coco butter, or mixtures thereof.

9. The composition of claim 1, wherein the composition further comprises a population of mesenchymal stem cells having at least one of the following characteristics when $0.7 \times 10^6$ of the cells are seeded into a 75 cm$^2$ flask and cultured for at least 96 hours: (a) the cells produce at least 4.5 mM of lactate within 24 hours of media exchange; and (b) the cells produce at least 150 pg/ml of GRO/KC within 24 hours of media exchange.

10. The composition of claim 1, wherein the composition further comprises one or more local anesthetic.

11. The composition of claim 1, wherein the composition further comprises from 0.001% to 5.00% (w/v) of one or more isotonic agent, wherein the isotonic agent is at least one member selected from the group consisting of a salt, a sugar or sugar alcohol, and an amino acid, or mixtures thereof.

12. The composition of claim 1, wherein the composition further comprises
at least one of a conditioning agent at a concentration ranging from 0.01% to 30% (w/v), a rheology modifier at a concentration ranging from 0.01% to 5% (w/v), and a surfactant at a concentration ranging from 0.01% to 6% (w/v).

13. The composition of claim 1, wherein the conditioned medium contains at least 4000 pg/ml of VEGF; at least 1000 pg/ml of GRO/KC; at least 750 pg/ml of TGF-β1; and at least 250 pg/ml of TGF-β2.

14. The composition of claim 12, wherein when present, the rheology modifier is a cellulose derivative, a polyvinyl alcohol (PVA) or glycerin, or mixtures thereof; wherein when present, the conditioning agent is hyaluronic acid, propylene glycol or sorbitol, or mixtures thereof; and wherein when present, the surfactant is polysorbate or glyceride, or mixtures thereof.

15. The composition of claim 12, wherein the composition further comprises from about 0.001% to about 5.00% (w/v) of one or more isotonic agent, wherein the isotonic agent is at least one member selected from the group consisting of a salt, a sugar or sugar alcohol, and an amino acid, or mixtures thereof.

16. The composition of claim 1, wherein the stem cells that condition the culture medium exhibit positive expression of CD29 and CD44 markers and negative expression of CD11b and CD45 markers; and wherein the stem cells that condition the culture medium exhibit a normal diploid karyotype.

17. The composition of claim 1, wherein the composition further comprises one or more conditioning agent present at a concentration ranging from 0.1 to 30% (w/v), and wherein the conditioning agent is Hyaluronic acid.

18. A face mask comprising on a surface thereof the composition of claim 1.

19. A skin patch comprising on a surface thereof the composition of claim 1, wherein the composition further contains Hyaluronic acid as a conditioning agent at a concentration of at least 0.02% (w/v).

20. A cell-free composition comprising:
a mesenchymal stem cell conditioned medium, wherein the conditioned medium contains VEGF at a concentration of at least 4000 pg/ml, TGF-β1 at a concentration of at least 67 pg/ml, and TGF-β2 at a concentration of at least 170 pg/ml,
wherein the composition further comprises at least one of a conditioning agent at a concentration ranging from 0.01% to 30% (w/v) and a rheology modifier at a concentration ranging from 0.01% to 5% (w/v).

21. The composition of claim 20, wherein the conditioned medium further contains at least 460 pg/ml of GRO/KC and at least 18 pg/ml of IP-10.

22. The composition of claim 21, wherein the composition further comprises one or more antimicrobial agent present at a concentration ranging from 0.001% to 1.0% (w/v).

23. The composition of claim 21, wherein the composition further comprises at least one member selected from the group consisting of a buffering agent, pH adjusting agent, a preservative, a surfactant, a foaming agent, a colorant, one or more acceptable carrier, and a chelating agent.

24. The composition of claim 21, wherein the composition further comprises from 0.001% to 5.00% (w/v) of one or more isotonic agent.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Forward PCR primer for human COX1

<400> SEQUENCE: 1
tagacatcgt actacacgac acg                                             23

<210> SEQ ID NO 2
<211> LENGTH: 20

<212> TYPE: DNA
<213> ORGANISM: Artificial Sequence
<220> FEATURE:
<223> OTHER INFORMATION: Reverse PCR primer for human COX1

<400> SEQUENCE: 2
tccaggttta tggagggttc                                              20

<210> SEQ ID NO 3
<211> LENGTH: 22
<212> TYPE: DNA
<213> ORGANISM: Artificial Sequence
<220> FEATURE:
<223> OTHER INFORMATION: Forward PCR primer for rat COX1

<400> SEQUENCE: 3
cggccaccca gaagtgtaca tc                                           22

<210> SEQ ID NO 4
<211> LENGTH: 22
<212> TYPE: DNA
<213> ORGANISM: Artificial Sequence
<220> FEATURE:
<223> OTHER INFORMATION: Reverse PCR primer for rat COX1

<400> SEQUENCE: 4
ggctcgggtg tctacatcta gg                                           22

<210> SEQ ID NO 5
<211> LENGTH: 20
<212> TYPE: DNA
<213> ORGANISM: Artificial Sequence
<220> FEATURE:
<223> OTHER INFORMATION: Forward PCR primer for human VN1R1

<400> SEQUENCE: 5
tggtctgggc cagtggctcc                                              20

<210> SEQ ID NO 6
<211> LENGTH: 25
<212> TYPE: DNA
<213> ORGANISM: Artificial Sequence
<220> FEATURE:
<223> OTHER INFORMATION: Reverse PCR primer for human VN1R1

<400> SEQUENCE: 6
gagtgttttc cttgtcctgc aggca                                        25

<210> SEQ ID NO 7
<211> LENGTH: 25
<212> TYPE: DNA
<213> ORGANISM: Artificial Sequence
<220> FEATURE:
<223> OTHER INFORMATION: Forward PCR primer for rat VN1R1

<400> SEQUENCE: 7
agaagagtta ctggcccaag ggaca                                        25

<210> SEQ ID NO 8
<211> LENGTH: 20
<212> TYPE: DNA
<213> ORGANISM: Artificial Sequence
<220> FEATURE:
<223> OTHER INFORMATION: Reverse PCR primer for rat VN1R1

<400> SEQUENCE: 8
ggggctgaac gctgggaagc 20